US007540930B2

(12) United States Patent
Moriuchi et al.

(10) Patent No.: US 7,540,930 B2
(45) Date of Patent: Jun. 2, 2009

(54) STENT TO BE IMPLANTED IN HUMAN BODY AND METHOD OF PRODUCING STENT

(75) Inventors: Yousuke Moriuchi, Fujinomiya (JP); Takeshi Kudou, Fujinomiya (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 150 days.

(21) Appl. No.: 11/583,088

(22) Filed: Oct. 19, 2006

(65) Prior Publication Data
US 2007/0033789 A1   Feb. 15, 2007

Related U.S. Application Data

(62) Division of application No. 10/274,943, filed on Oct. 22, 2002, now abandoned.

(30) Foreign Application Priority Data
Oct. 22, 2001   (JP) .............................. 2001-323531

(51) Int. Cl.
*C22F 1/10*   (2006.01)
(52) U.S. Cl. ...................... 148/519; 148/525; 148/563
(58) Field of Classification Search ........................ None
See application file for complete search history.

(56) References Cited

U.S. PATENT DOCUMENTS

| 5,383,892 | A |   | 1/1995 | Cardon et al. |
| 5,776,162 | A |   | 7/1998 | Kleshinski |
| 5,782,741 | A | * | 7/1998 | Bradshaw et al. ............ 600/3 |
| 5,853,419 | A |   | 12/1998 | Imran |
| 5,879,381 | A | * | 3/1999 | Moriuchi et al. ........... 623/1.16 |
| 6,042,606 | A |   | 3/2000 | Frantzen |
| 6,168,621 | B1 |  | 1/2001 | Vrba |
| 6,264,687 | B1 |  | 7/2001 | Tomonto |
| 6,315,708 | B1 |  | 11/2001 | Salmon et al. |
| 6,485,507 | B1 |  | 11/2002 | Walak et al. |

FOREIGN PATENT DOCUMENTS

| WO | WO 96/03092 A1 | 2/1996 |
| WO | WO 98/58600 A1 | 12/1998 |
| WO | WO 99/16387 A1 | 4/1999 |
| WO | WO 00/44946 A1 | 8/2000 |
| WO | WO 00/71054 A1 | 11/2000 |
| WO | WO 01/41675 A1 | 6/2001 |

* cited by examiner

*Primary Examiner*—George Wyszomierski
(74) *Attorney, Agent, or Firm*—Buchanan Ingersoll & Rooney PC

(57) ABSTRACT

A stent, to be implanted in a human body, is made of a super-elastic metal which is formed approximately cylindrically and integrally and which shows super-elasticity before and after said stent is inserted into said human body. The stent has a plurality of annular parts (expansion element) deformable in a direction in which an outer diameter thereof contracts, when a stress is applied thereto and a plurality of connection parts (connection element) each connecting said adjacent annular parts to each other, with said annular parts arranged in an axial direction of said stent. Each of said annular parts is elastically deformable owing to super-elasticity thereof, whereas each of said connection parts is substantially a plastically deformable part not super-elastic entirely or partly.

7 Claims, 16 Drawing Sheets

F I G. 2
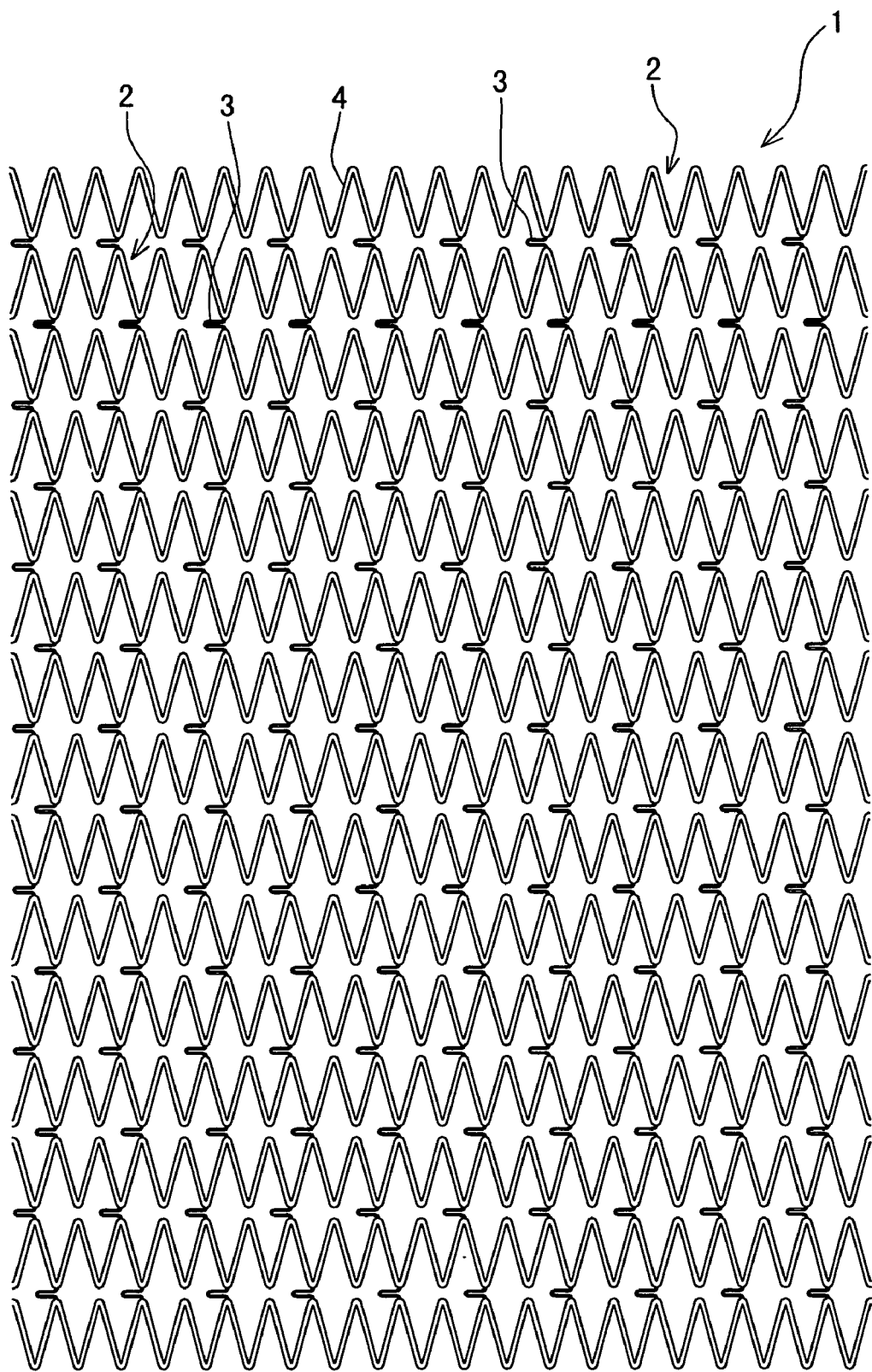

F I G. 3
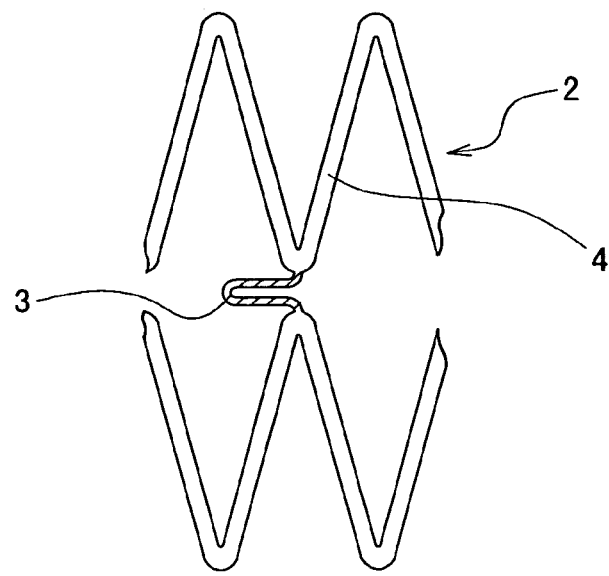
F I G. 4
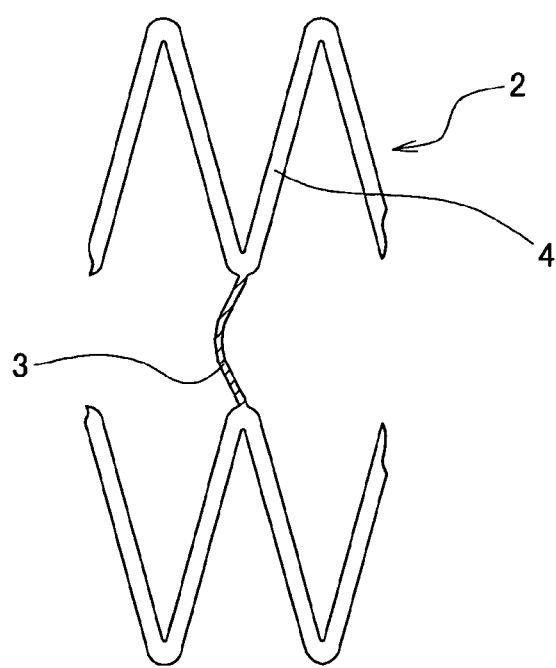

F I G. 7
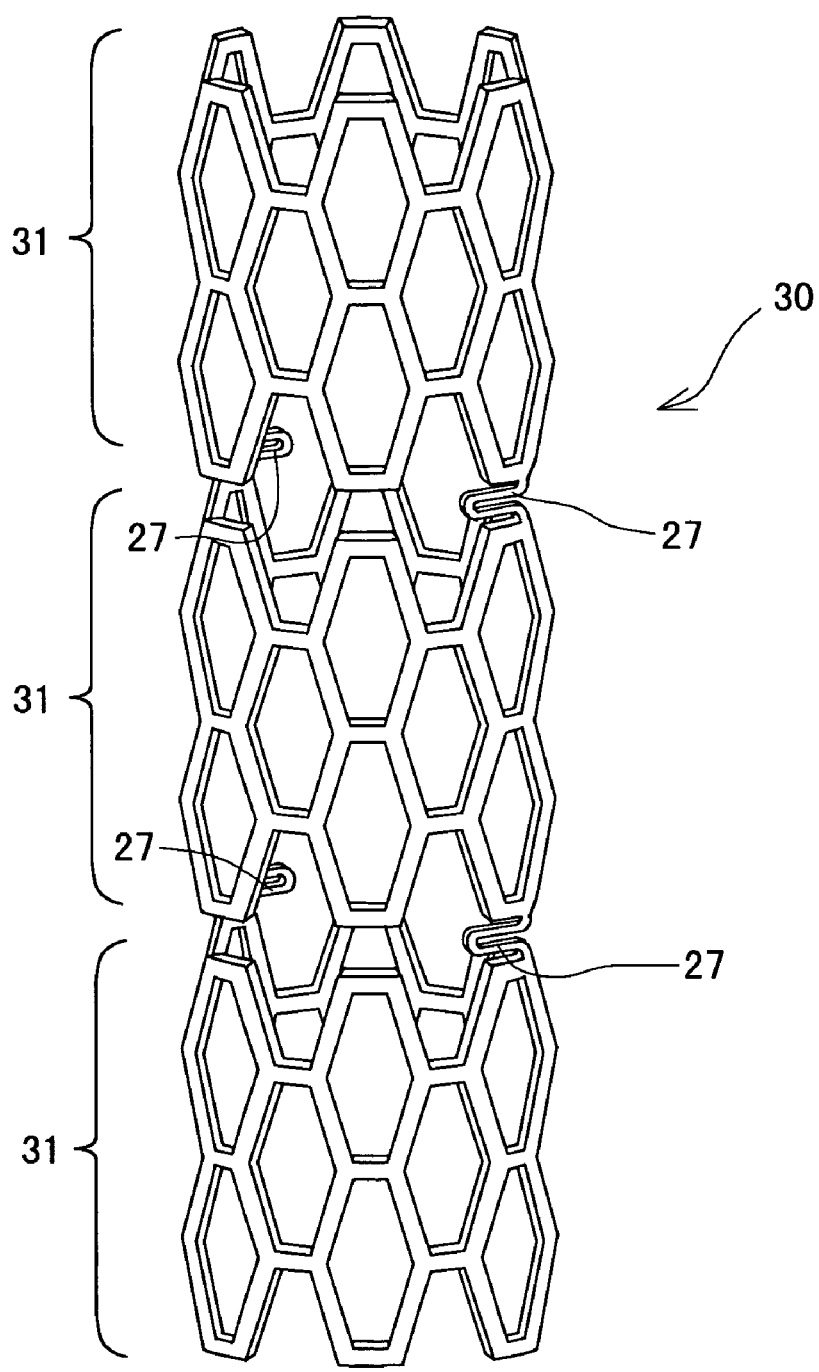

F I G. 13
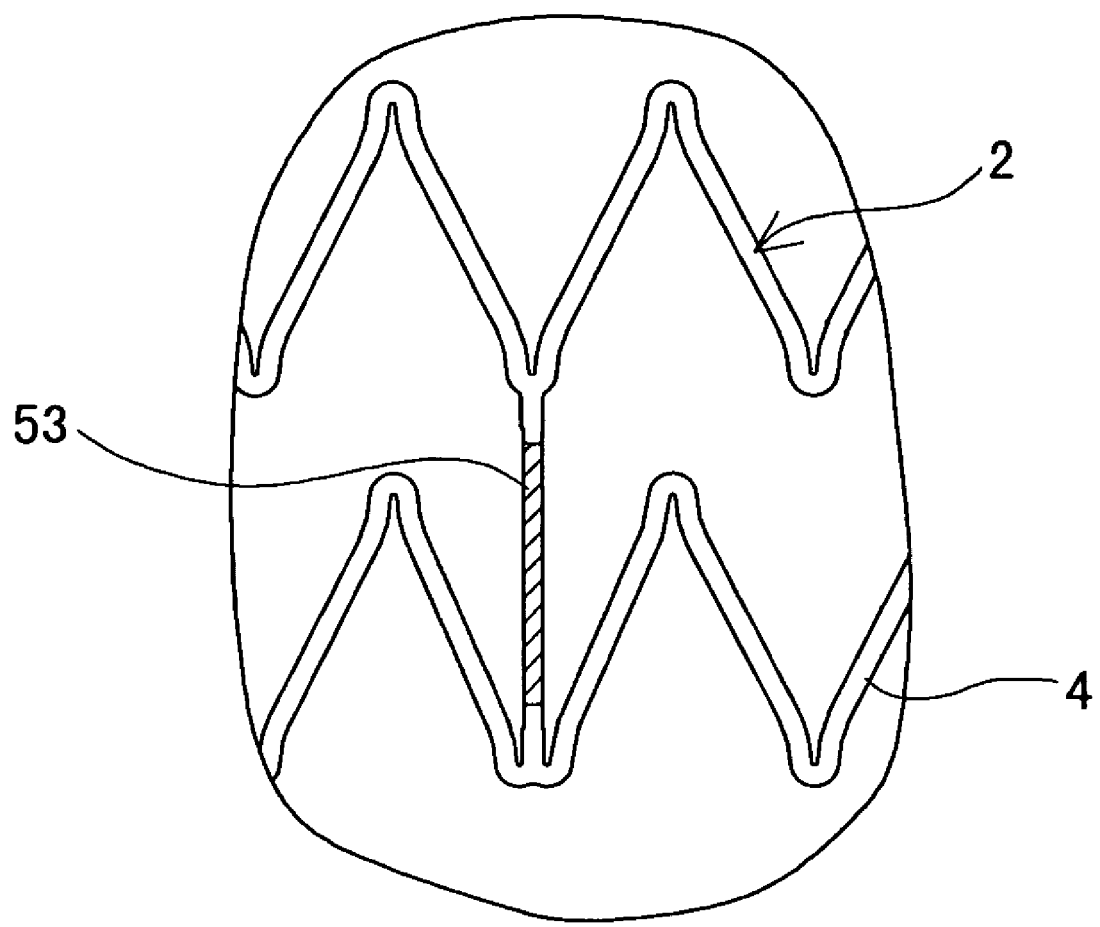

F I G. 16
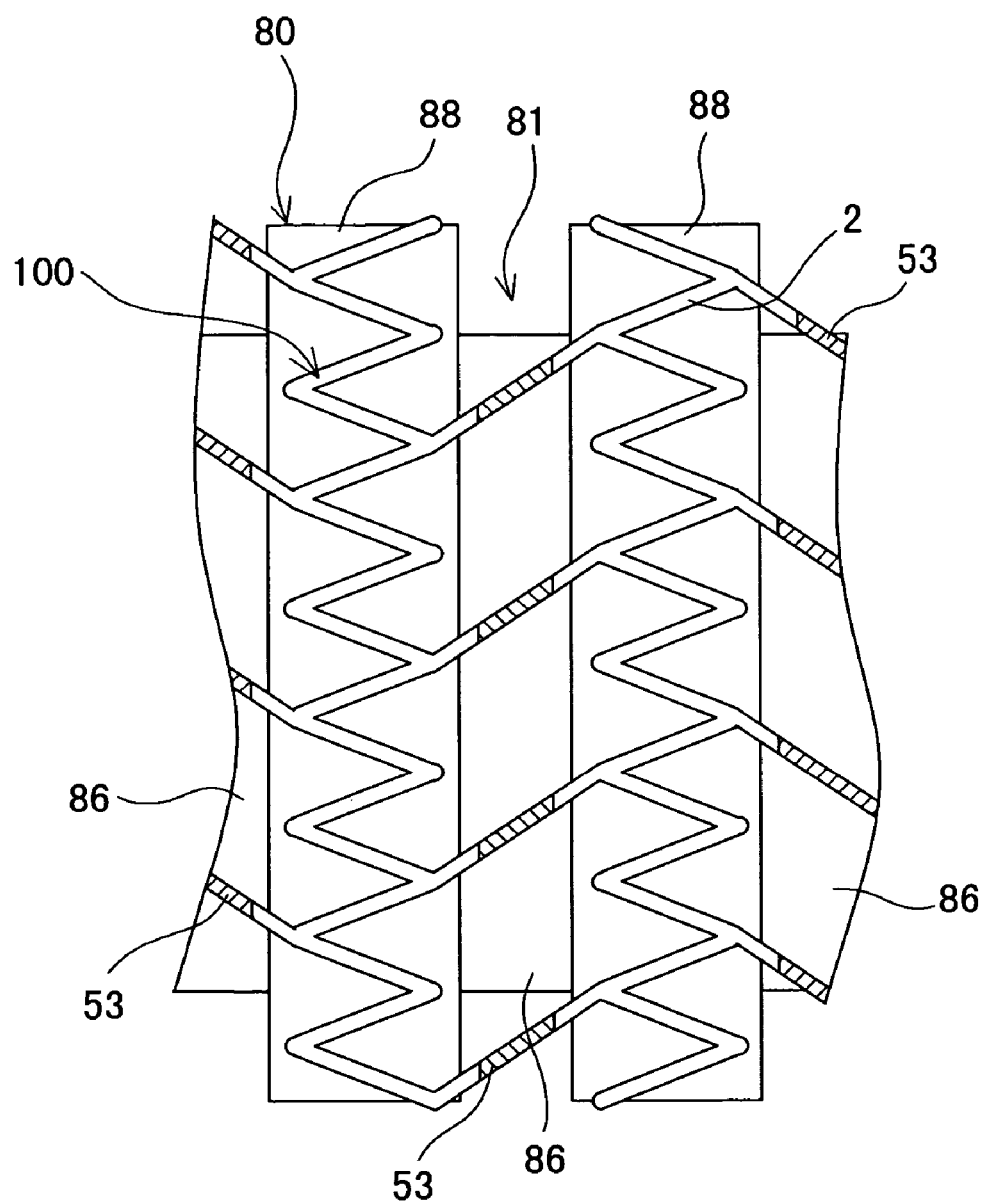

STENT TO BE IMPLANTED IN HUMAN BODY AND METHOD OF PRODUCING STENT

This application is a divisional of U.S. application Ser. No. 10/274,943 filed on Oct. 22, 2002, now abandoned, for which a claim for priority under 35 U.S.C. § 120 is made. The entire content of U.S. application Ser. No. 10/274,943 is incorporated herein by reference.

BACKGROUND OF THE INVENTION

The present invention relates to a stent that is implanted in lumens such as the blood vessel, the bile duct, the trachea, the esophagus, the ureter, and the like so that it is used to improve a stenosed portion or a closed portion generated in the lumens.

To cure various diseases that are caused when the blood vessel or lumens in the human body are stenosed or closed, the stent which is a tubular medical appliance is implanted at the stenosed portion or the closed portion to expand them and secure the lumen thereof. Because the stent is inserted into the human from outside, its diameter is small. The stent is dilated or returned to its original shape to make its diameter large at the stenosed or closed portions to keep the dilated state of the lumen.

The stent is classified into a self-expandable stent and a balloon expandable stent, depending on the function and dilating mode thereof.

The balloon expandable stent which itself has no dilating function is inserted into a desired portion. Then, a balloon provided in the stent is inflated to dilate (plastically deform) the stent so that the stent is fixed to the inner surface of the desired lumen, with the stent in close contact therewith. That is, it is necessary to dilate the stent of this type in implanting it in the desired portion.

Fundamentally, the self-expandable stent is made of an elastic material. The final size of the self-expandable stent is set when it is expanded. In introducing the self-expandable stent into the human body, it is folded into a small size and put into a member (plastic tube in most cases) restricting its configuration. Then the member, namely, the tube is introduced into the human body. The self-expandable stent is discharged from the tube at the desired portion. The self-expandable stent dilates itself owing to its elasticity.

The dilating mode of the balloon expandable stent and that of the self-expandable stent are different from each other. The characteristic of the balloon expandable stent and that of the self-expandable stent are also different from each other. These two kinds of the stents have merits and demerits. The balloon expandable stent dilates in the form of a plastic deformation in conformity to the dilation of the balloon. Therefore the balloon expandable stent can be embedded in a curved blood vessel, with the balloon expandable stent curved plastically. However, in the case where the balloon expandable stent is embedded in a sublimis blood vessel (artery near the surface of human body such as carotid arteries, femoral artery, and the like), there is a fear that the balloon expandable stent is deformed plastically by an external force. Generally, embedded into such a portion is the self-expandable stent that is capable of returning to its original configuration by its elasticity, even though it is deformed by an external force applied thereto. The self-expandable stent has property of returning to its original configuration. In most cases, the stent is formed straight in its longitudinal direction. Thus even though the self-expandable stent is so configured that it can be curved at a light force, it will return to its original (straight) configuration in the human body. Therefore when the self-expandable stent is implanted in a curved blood vessel, the force of the self-expandable stent of returning to its original straight shape is always applied to both ends thereof.

The self-expandable stent is disclosed in U.S. Pat. No. 6,042,606 (WO99/16,387). The stent disclosed therein is formed straight in its longitudinal direction. Thus even though the self-expandable stent is so configured that it can be curved at a light force, it will return to its original (straight) configuration in the human body. Therefore when the self-expandable stent is implanted in a curved blood vessel, the force of the self-expandable stent of returning to its original straight shape is always applied to both ends thereof.

SUMMARY OF THE INVENTION

Therefore, it is an object of the present invention to provide a stent of a self-expandable type to which little stress is applied to both ends thereof after it is implanted in the blood vessel of the human body.

According to a first aspect of the invention, there is provided a stent, to be implanted in a human body, made of a super-elastic metal which is formed approximately cylindrically and integrally and which shows super-elasticity before and after said stent is inserted into said human body; said stent having a plurality of annular parts deformable in a direction in which an outer diameter thereof contracts, when a stress is applied thereto and a plurality of connection parts each connecting said adjacent annular parts to each other, with said annular parts arranged in an axial direction of said stent, wherein each of said annular parts is elastically deformable owing to super-elasticity thereof, whereas said connection part is substantially a plastically deformable part not super-elastic entirely or partly or a normal elastically deformable part not super-elastic entirely or partly.

According to a second aspect of the invention, there is provided a method of producing a stent to be implanted in a human body, comprising the steps of: forming a base material for said stent having a plurality of annular parts deformable in a direction in which an outer diameter thereof contracts, when a stress is applied thereto and a plurality of connection parts each connecting said adjacent annular parts to each other, with said annular parts arranged in an axial direction of said stent, by partly removing a side surface of a prepared approximately cylindrical pipe, made of a super-elastic metal, having an outer diameter suitable for a portion of the human body in which said stent is implanted; and heat-treating a part or an entirety of said connection part of said base material for said stent to substantially eliminate super-elasticity of said connection part and impart plastic deformability or normal elasticity thereto.

According to a third aspect of the invention, there is provided a method of producing a stent to be implanted in a human body, comprising the steps of: forming a base material for said stent having a plurality of annular parts and a plurality of connection parts each connecting said adjacent annular parts to each other, with said annular parts arranged in an axial direction of said stent by preparing an approximately cylindrical metal pipe having an outer diameter smaller than an inner diameter of a portion in which said stent is implanted and having super-elasticity or a shape memory characteristic or to which said super-elasticity or said shape memory characteristic can be imparted and by partly removing a side surface of said pipe; forming an expanded mode of said base material for said stent by expanding said base material for said stent so that an outer diameter thereof becomes suitable for said portion in which said stent is implanted and by heat-setting said base material for said stent in an expanded state to store a configuration of said expanded base material for said stent and allow said super-elasticity to appear; and heat-treating said expanded base material for said stent by heating an entirety or a portion of said connection part to eliminate super-elasticity thereof substantially and impart plastic deformability or normal elasticity thereto.

BRIEF DESCRIPTION OF THE DRAWINGS

FIG. 2 is a development view showing the stent shown in FIG. 1.

FIG. 3 is a partly enlarged view showing the stent shown in FIG. 1.

FIG. 4 is an explanatory view showing a state in which a connection part of the stent shown in FIG. 3 has been stretched.

FIG. 7 is perspective view showing a stent according to another embodiment of the present invention.

FIG. 13 is a partly enlarged view showing the stent shown in FIG. 11.

FIG. 16 shows a state in which a base material for the stent is mounted on the heat sink shown in FIG. 15.

DESCRIPTION OF THE PREFERRED EMBODIMENTS

Figure 1:
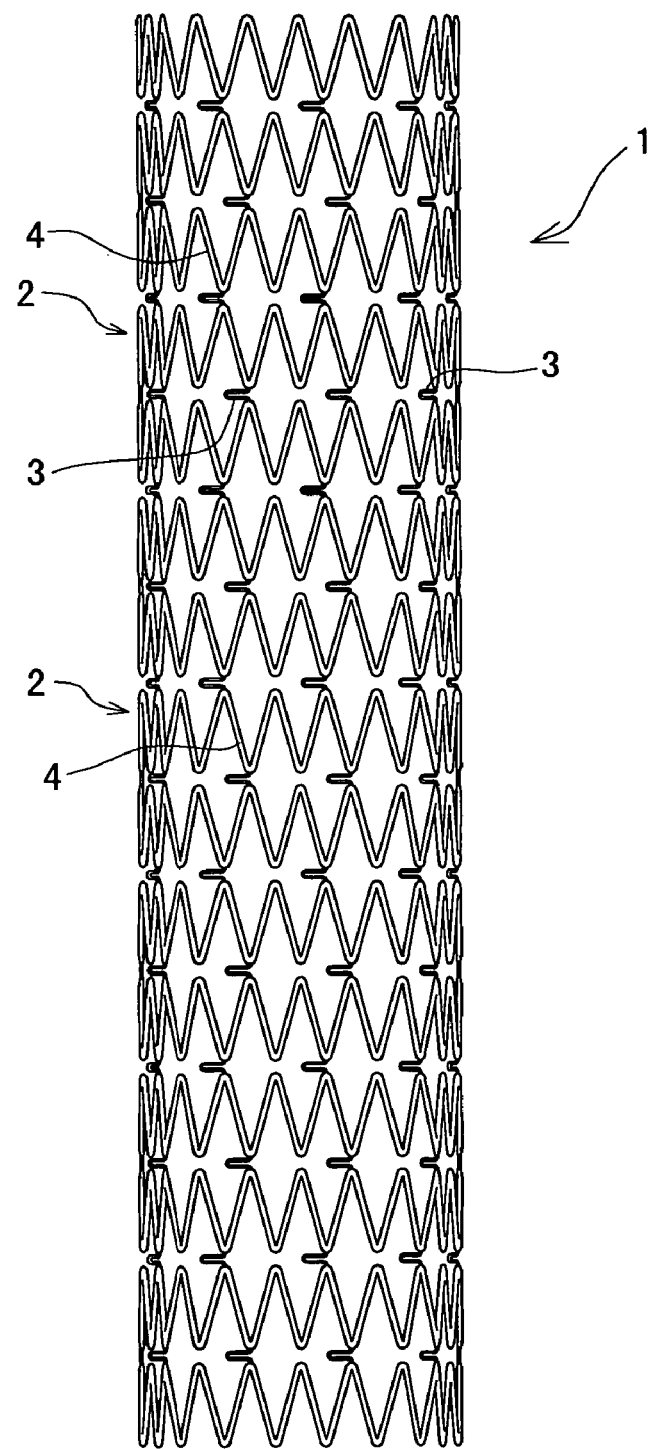
FIG. 1 is a front view showing a stent according to an embodiment of the present invention.

The stent of an embodiment of the present invention will be described below with reference to the drawings.

A stent 1 of the present invention is implanted in a human body. The stent 1 is made of a super-elastic metal formed approximately cylindrically and integrally. The super-elastic metal shows super-elasticity before and after the stent 1 is inserted into the human body. The stent 1 has a plurality of annular parts 2 (in other words, expansion element) deformable in a direction in which an outer diameter thereof contracts, when a stress is applied thereto and a plurality of connection parts 3 (in other words, connection element) each connecting the adjacent annular parts 2 to each other, with the annular parts 2 arranged in the axial direction of the stent 1. The annular part 2 is elastically deformable owing to its super-elasticity. The connection part 3 is substantially a plastically deformable part not super-elastic entirely or partly or a normal elastically deformable part not super-elastic entirely or partly.

The connection part 3 has a plastically deformable part or a normal elastically deformable part.

The stent 1 of the embodiment is an integral product having a plurality of the annular parts 2 arranged in the axial direction of the stent 1 and a plurality of the connection parts 3 each connecting the adjacent annular parts 2 to each other.

Figure 5:
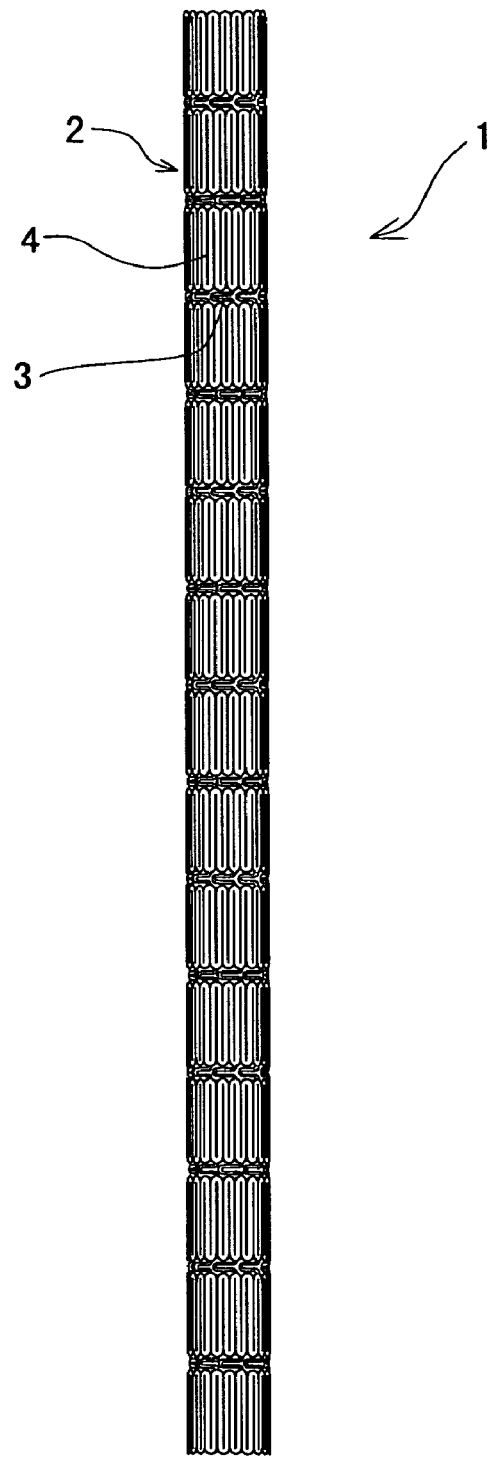
FIG. 5 is a front view showing a state in which the stent shown in FIG. 1 has been contracted.

As shown in FIGS. 1 and 2, the annular parts 2 formed of the super-elastic metal showing the super-elasticity are arranged almost linearly. Each annular part 2 has a deformation assistant function of assisting the deformation of the stent 1 in the direction in which the outer diameter thereof contracts, when a stress is applied to the stent 1. The adjacent annular parts 2 are connected to each other with the connection parts 3 constituting the plastically deformable part or having the plastically deformable part. The connection parts 3 may constitutes the plastically deformable part or has the plastically deformable part. As shown in FIG. 5, the diameter of the stent 1 of the embodiment contracts, when a load is applied radially inwardly to the entire side (peripheral) surface thereof.

As shown in FIGS. 1, 2, and 3, the stent 1 of the embodiment has a plurality of the annular parts 2 each composed of a linear material 4 that is wavy (zigzag) and annular and functions to keep the stent 1 expanded. The annular parts 2 are connected to one another with the connection parts 3 (connector) in such a way that the adjacent annular parts 2 do not separate from each other. A plurality of the annular parts 2 are arranged almost linearly in the axial direction of the stent 1, with valleys and mountains of the axially adjacent wavy annular parts 2 proximate to each other.

As described above, the annular part 2 is composed of the linear material 4 wavy (zigzag) and annular. Thus the annular parts 2 has the deformation assistant function of assisting the deformation of the stent 1 in the direction in which the outer diameter thereof contracts, when a stress is applied to the stent 1. Further the annular part 2 is made of the super-elastic metal showing the super-elasticity. Thus the annular part 2 returns to the original configuration, when the stress is eliminated therefrom.

Unlike the annular part 2, the connection part 3 is not substantially super-elastic entirely or partly and is plastically deformable or normal elastically deformable. Each of the connection parts has a plastically deformable part or a normal elastically deformable part. But some of he connection parts may have a plastically deformable part or a normal elastically deformable part. Thereby the stent 1 is capable of plastically deformable or normal elastically deformable at the connection part 3. Further the connection part 3 reduces a stress applied to a lumen such as a blood vessel by both ends of the stent 1, when the stent 1 is implanted therein. Since the connection part 3 is plastically deformable or normal elastically deformable, the connection part 3 is curved in conformity to a curvature of the blood vessel and keeps its curved configuration when the stent 1 is implanted in a curved blood vessel or the like. Therefore little load is applied to both ends of the stent 1. FIG. 3 is an enlarged view showing the neighborhood of the connection part 3 of the stent 1. The connection part 3 (portion shown with oblique lines) shown in FIG. 3 deforms plastically or normal elastically. When the stent 1 is bent, with the connection part 3 (portion shown with oblique lines) disposed radially outward, the connection part 3 is stretched and deforms plastically as shown in FIG. 4. Consequently there is an increase in the interval between the adjacent annular parts 2 because the adjacent annular parts 2 are connected to each other with the stretched connection part 3. Since the connection part 3 deforms plastically, the connection part 3 keeps the stretched state. The occupation percentage of the plastically deformable portion (or normal elastically deformable portion) of the connection part 3 is favorably in the range of 10 to 100 and more favorably in the range of 40 to 100. The occupation percentage of the plastically deformable portion (or normal elastically deformable portion) of the connection part 3 is more favorably in the range of 50 to 100 and most favorably in the range of 80 to 100.

The connection part 3 of the stent 1 of the embodiment connects proximate valleys and mountains of the adjacent wavy annular parts 2 to each other and is curved or bent. Therefore, when a force is applied to the stent 1 in a curved direction after the stent 1 is implanted in the lumen, the stent 1 is capable of coping with the applied force without opposing thereto, because the connection part 3 is disposed radially outward and thus capable of stretching. Therefore little stress is applied to the lumen in which the stent 1 has been implanted. In the stent 1 of the embodiment, the connection part 3 is curved in the direction orthogonal to the axial direction of the stent 1. Therefore the connection part 3 is capable of reliably stretching, when the connection part 3 is curved. The connection part 3 does not necessarily have to be orthogonal to the axial direction of the stent 1, but may be curved or bent at a predetermined angle with respect to the axial direction of the stent 1. Although the connection part 3 of the embodiment is U-shaped, it may be V-shaped or S-shaped. In the case where the connection part 3 is bent or curved, it is preferable that a bent portion thereof or a curved portion thereof is essentially the plastically deformable portion (or normal elastically deformable portion).

In the stent 1 of the embodiment, the adjacent annular parts 2 are connected to each other with a plurality of the connection parts 3. It is preferable to connect the annular parts 2 to each other by a plurality of the connection parts 3. In this case, it is preferable to almost confront them at two positions of all the positions where the valleys and the mountains of the adjacent annular parts 2 confront each other. It is also preferable to dispose three or more connection parts 3, with the connection parts 3 forming an almost equal angle with respect to the axis of the stent 1. In the embodiment, valleys and mountains of the axially adjacent wavy annular parts 2 are proximately formed, with the valleys and the mountains connected to each other alternately by the connection parts 3. In the stent 1 of the embodiment, the connection part 3 is not disposed inside the annular part 2. Therefore in the stent 1, the annular parts 2 and the connection parts 3 are arranged in the axial direction thereof. In the stent 1 of this embodiment, a plurality of the annular parts 2 and a plurality of the connection parts 3 are alternately arranged in the axial direction thereof, with the annular parts 2 disposed at both ends of the arrangement. When the connection parts 3 are viewed from the side (peripheral) surface of the stent 1, the connection parts 3 are not disposed inside the annular parts 2, but disposed on an annular zone orthogonal to the axis of the stent 1. Therefore it is possible to treat a change in properties of the connection part 3 easily and reduce an influence given to the annular part 2 by the treatment of the change in properties of the connection part 3.

Although the outer diameter of the stent 1 is different according to a portion where the stent 1 is implanted, the outer diameter thereof is favorably in the range of 2.0 to 30 mm and more favorably in the range of 2.5 to 20 mm. The thickness of the stent 1 is favorably in the range of 0.04 to 1.0 mm and more favorably in the range of 0.06 to 0.5 mm. The length of the stent 1 is in the range of 10 to 150 mm and favorably in the range of 15 to 100 mm. In the case where the stent is implanted in a blood vessel, the outer diameter thereof is favorably in the range of 2.0 to 14 mm and more favorably in the range of 2.5 to 10 mm. The thickness of the stent is favorably in the range of 0.04 to 0.3 mm and more favorably in the range of 0.06 to 0.2 mm. The length of the stent is in the range of 5 to 40 mm and favorably in the range of 10 to 30 mm.

As described above, in the stent 1 of the embodiment, the annular part 2 is composed of a plurality of linear materials 4 wavy (zigzag) and annular. The number of waves is favorably in the range of 6 to 36 and more favorably in the range of 8 to 24. The length of the annular part 2 is favorably in the range of 1 to 10 mm and more favorably in the range of 1.5 to 5 mm. The number of the annular parts 2 is favorably in the range of 3 to 30 and more favorably in the range of 5 to 20. The distance between the adjacent annular parts 2, in other words, the length of the connection part 3 in the axial direction of the stent 1 is favorably in the range of 0.1 to 5 mm and more favorably in the range of 0.15 to 3 mm. It is favorable that the width of the linear material 4 constituting the connection part 3 is small to allow the linear material 4 to be bent at a small force. More specifically, the width of the linear material 4 constituting the connection part 3 is favorably in the range of 0.03 to 0.2 mm and more favorably in the range of 0.05 to 0.1 mm. The length of the connection part 3 is favorably in the range of 0.15 to 8 mm and more favorably in the range of 0.2 to 5 mm when the connection part 3 is straight.

The mode of the annular part of the stent is not limited to the above-described one.

Figure 6:
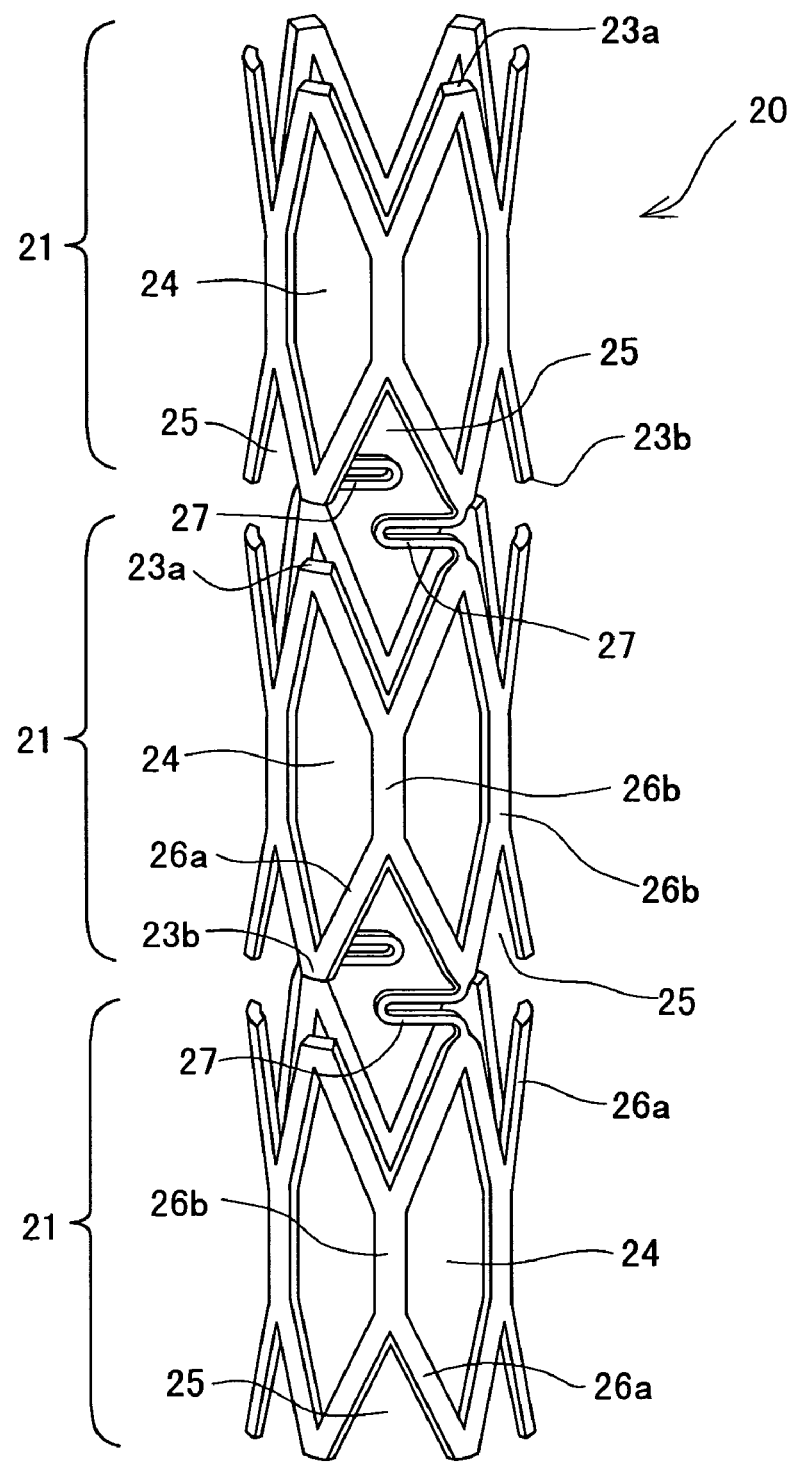
FIG. 6 is perspective view showing a stent according to another embodiment of the present invention.

For example, the stent may have the annular part having a form as shown in FIG. 6.

As in the case of the stent 1, a stent 20 of the embodiment is implanted in the human body and made of a super-elastic metal formed approximately cylindrically and integrally. The super-elastic metal shows super-elasticity before and after the stent 20 is inserted into the human body.

An annular part 21 of the stent 20 of the embodiment is composed of a linear constituent which has a plurality of notches and a plurality of openings formed on a side (peripheral) surface thereof and is made of a metal showing super-elasticity.

The stent 20 of the embodiment is also an integral product having a plurality of the annular parts 21 arranged in the axial direction of the stent 20 and a plurality of the connection parts 27 each connecting the adjacent annular parts 21 to each other.

The annular part 21 has the notch at its ends 23a and 23b. Thus the ends 23a and 23b of the annular part 21 are capable of deforming easily. In particular, a partial deformation of the end can be accomplished. Therefore the annular part 21 has a favorable response to a deformation of a blood vessel in which the stent is implanted. The end 23 is composed of ends of a plurality of frames 26a. Thus the end 23 has a sufficient strength and thus is not easily broken. An opening 24 surrounded with frames 26a and 26b is formed between both ends 23a and 23b of the annular part 21. The opening 24 is deformed easily by a deformation of the frame 26a. Therefore the annular part 21 deforms easily at its central portion (central portion of frame).

In this embodiment, the opening 24 has the shape of a hexagon long in the axial direction of the stent 20. The notch 25 has the shape of an isosceles triangle. A plurality of the notches 25 are formed at each end of the annular part 21. More specifically, six notches 25 having almost the same configuration are formed at each end of the annular part 21. A plurality of the openings 24 are formed in such a way as to form the side surface of the stent 20 or the peripheral surface thereof. More specifically, six openings 24 are formed. Neither the configuration of each of the notch and the opening is limited to the above-described one nor the number of each of the notch and the opening is limited to the above-described one. It is preferable that the number of the notches is 3 to 10 and that the number of the openings is also 3 to 10.

In the stent 20 of the embodiment, a plurality of the annular parts 21 are arranged in the axial direction thereof. The adjacent annular parts 21 are connected to each other with the connection parts 27. The connection part 27 is substantially a plastically deformable part (or normal elastically deformable part) not super-elastic entirely or partly. In other words, the connection part 27 constitutes the substantially plastically deformable part (or normal elastically deformable part) or has the plastically deformable part (or normal elastically deformable part).

In the stent 20 of the embodiment, three annular parts 21 are linearly arranged and connected to each other by the connection parts 27. The connection part 27 connects proximate apexes of the adjacent annular parts 21 to each other and is curved or bent. Therefore, when a force is applied to the stent 20 in a curved direction after the stent 20 is implanted in the lumen, the stent 20 is capable of coping with the applied force without opposing thereto, because the connection part 27 is disposed radially outward and thus capable of stretching. Therefore little stress is applied to the lumen in which the stent 20 has been implanted. In the stent 20 of the embodiment, the connection part 27 is curved in the direction orthogonal to the axial direction of the stent 20. Therefore the connection part 27 is capable of reliably stretching, when the connection part 27 is curved. The connection part 27 does not necessarily have to be orthogonal to the axial direction of the stent 20, but may be curved or bent at a predetermined angle with respect to the axial direction of the stent 20. Although the connection part 27 of the embodiment is U-shaped, it may be V-shaped or S-shaped. In the case where the connection part 27 is bent or curved, it is preferable that a bent portion thereof or a curved portion thereof is essentially the plastically deformable portion. The occupation percentage of the plastically deformable portion (or normal elastically deformable portion) of the connection part 27 is favorably in the range of 10 to 100 and more favorably in the range of 40 to 100. The occupation percentage of the plastically deformable portion (or normal elastically deformable portion) of the connection part 27 is more favorably in the range of 50 to 100 and most favorably in the range of 80 to 100.

In the stent 20 of the embodiment, the adjacent annular parts 21 are connected to each other with a plurality of the connection parts 27. It is preferable to connect the annular parts 21 to each other with a plurality of the connection parts 27. In this case, it is preferable to almost confront them at two positions of all the positions where the adjacent annular parts 21 confront each other. It is also preferable to dispose three or more connection parts 27, with the connection parts 27 forming an almost equal angle with respect to the axis of the stent 20. In the embodiment, the connection parts 27 are confronted at two positions of all the positions where the adjacent annular parts 21 confront each other.

In the stent 20 of the embodiment, the connection part 27 is not disposed inside the annular part 21. Therefore in the stent 20, the annular parts 21 and the connection parts 27 are arranged in the axial direction thereof. In the stent 20 of this embodiment, a plurality of the annular parts 21 and a plurality of the connection parts 27 are alternately arranged in the axial direction thereof, with the annular parts 21 disposed at both ends of the arrangement. When the connection parts 27 are viewed from the side (peripheral) surface of the stent 20, the connection parts 27 are not disposed inside the annular parts 21, but disposed on an annular zone orthogonal to the axis of the stent 20. Therefore it is possible to treat a change in properties of the connection part 27 easily and reduce an influence given to the annular part 21 by the treatment of the change in properties of the connection part 27.

The length of the annular part 21 of the stent 20 of the embodiment is favorably in the range of 2 to 4 mm and more favorably in the range of 2.5 to 3.5 mm. The number of the annular parts 21 is favorably in the range of 3 to 30 and more favorably in the range of 5 to 20. The distance between the adjacent annular parts 21, in other words, the length of the connection part 27 in the axial direction of the stent 20 is favorably in the range of 0.1 to 5 mm and more favorably in the range of 0.15 to 3 mm. It is favorable that the width of the linear material (frame) constituting the annular part 21 is favorably in the range of 0.08 to 0.3 mm and more favorably in the range of 0.1 to 0.2 mm. The length of the connection part 27 is favorably in the range of 0.15 to 8 mm and more favorably in the range of 0.2 to 5 mm when the connection part 27 is straight. It is favorable that the width of the linear material constituting the connection part 27 is small to allow the linear material to be bent at a small force. More specifically, the width of the linear material constituting the connection part 27 is favorably in the range of 0.03 to 0.2 mm and more favorably in the range of 0.05 to 0.1 mm.

As shown in FIG. 7, according to another embodiment of the present invention, a stent 30 may have annular parts 31 each having trapezoidal notches formed at its both ends and a plurality of hexagonal openings formed at its central portion in the shape of a honeycomb. As in the case of the above-described embodiments, a connection part 27 is plastically deformable partly or entirely.

The mode of the annular part is not limited to the above-described one.

Figure 8:
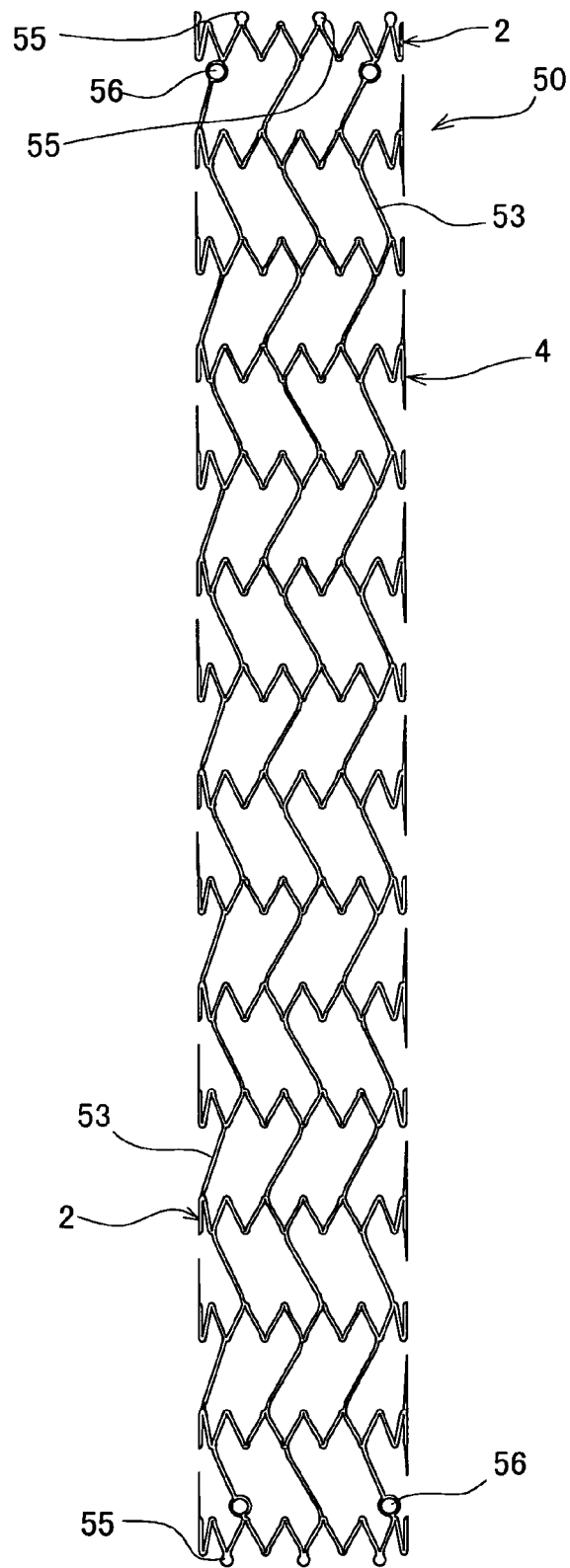
FIG. 8 is a front view showing a stent according to an embodiment of the present invention.
Figure 9:
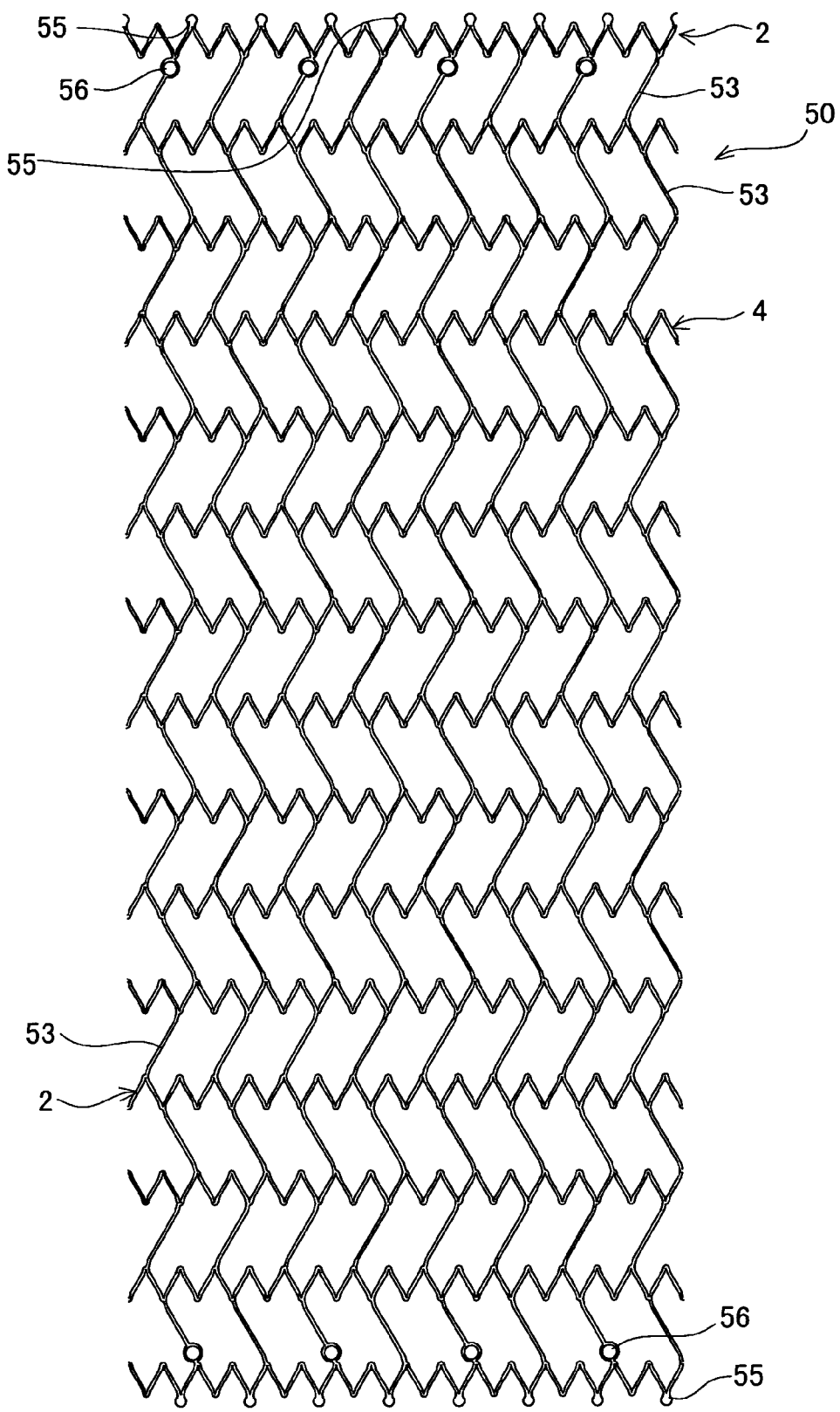
FIG. 9 is a development view showing the stent shown in FIG. 8.
Figure 10:
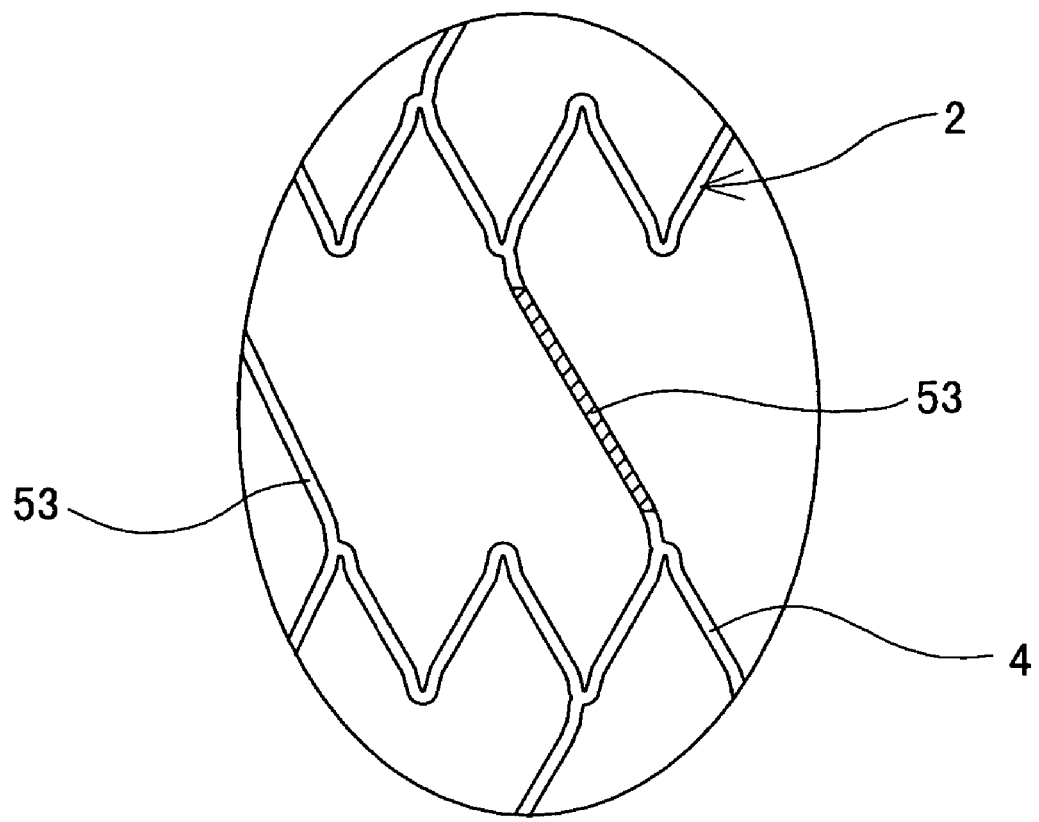
FIG. 10 is a partly enlarged view showing the stent shown in FIG. 8.

FIG. 8 is a front view showing a stent according to an embodiment of the present invention. FIG. 9 is a development view showing the stent shown in FIG. 8. FIG. 10 is a partly enlarged view showing the stent shown in FIG. 8.

As shown in FIGS. 8 and 9, a stent 50 of the embodiment has a plurality of the annular parts 2 each composed of a linear material 4 that is wavy (zigzag) and annular and functions to keep the stent 50 expanded. The annular parts 2 are connected to each other with the connection parts 53 (connector) in such a way that the adjacent annular parts 2 do not separate from each other. A plurality of the annular parts 2 are arranged almost linearly in the axial direction of the stent 50, with valleys and mountains of the axially adjacent wavy annular parts 2 confronting each other.

The connection part 53 is not substantially super-elastic entirely or partly and is plastically deformable or normal elastically deformable. Thereby the stent 50 is capable of plastically deformable or normal elastically deformable at the connection part 53. Further the connection part 53 reduces a stress applied to a lumen such as a blood vessel by both ends of the stent 50, when the stent 50 is implanted therein. Since the connection part 53 is plastically deformable or normal elastically deformable, the connection part 53 is curved in conformity to a curvature of the blood vessel and keeps its curved configuration when the stent 50 is implanted in a curved blood vessel or the like. Therefore little load is applied to both ends of the stent 50. FIG. 10 is an enlarged view showing the neighborhood of the connection part 53 of the stent 50. The connection part 53 (portion shown with oblique lines) shown in FIG. 10 deforms plastically or has a normal elastic deformation. When the stent 50 is bent, the connection part 53 deforms plastically or normal elastically. The occupation percentage of the plastically deformable portion (or normal elastically deformable portion) of the connection part 53 is favorably in the range of 10 to 100 and more favorably in the range of 40 to 100. The above-described normal elastic deformation means an elastically deformed state not reaching the super-elastic.

The connection part 53 of the stent 50 of the embodiment connects proximate valleys and mountains of the adjacent wavy annular parts 2 to each other. The connection part 53 is straight. In the stent of the embodiment, each connection part 53 connects the valley of the annular part 2 to the mountain adjacent to the mountain, of the adjacent annular part 2, nearest to the valley. Thus the connection part 53 inclines. That is, the connection part 53 inclines at a predetermined angle to the axis of the stent 50.

In the stent 50 of the embodiment, the adjacent annular parts 2 are connected to each other by a plurality of the connection parts 53. It is preferable to connect the annular parts 2 to each other with a plurality of the connection parts 53. In the case where the connection parts 53 are formed at two positions, it is preferable to confront them at two positions of all the positions where the valleys and the mountains of the adjacent annular parts 2 almost confront each other. It is also preferable to dispose three or more connection parts 53, with the connection parts 53 forming an almost equal angle with the axis of the stent 50. In the embodiment, a plurality of valleys and mountains are formed on the axially adjacent wavy annular parts 2, with the valleys and the mountains proximate to each other. The valleys and the mountains are connected to each other alternately by the connection parts 53. The valley of the annular part 2 is connected to the mountain adjacent to the mountain, of the adjacent annular part 2, nearest to the valley. The connection parts 53 connecting the same adjacent annular parts 2 to each other are parallel with each other. The connection part 53 adjacent to each other in the axial direction of the stent 50 connects the valleys to each other alternately. The connection parts 53 adjacent to each other in the axial direction of the stent 50 incline in different directions. As shown in FIG. 9, the connection part 53 disposed uppermost incline left downward, whereas the connection part 53 disposed below it incline right downward. In the stent 50 of the embodiment, the connection part 53 and the straight portion of the annular part 2 connected with the connection part 53 form a zigzag line in the axial direction of the stent 50. In the stent 50 of the embodiment, the connection part 53 is not disposed inside the annular part 2.

More specifically, in the stent 50 shown in FIGS. 8 and 9, the number of the zigzag lines of each annular part 2 is 16. The connection part 53 is formed at eight positions, with the connection parts 53 forming an equal angle to the axis of the stent 50. In the stent 50, a plurality of the annular parts is formed, with the mountains and the valleys adjacent to each other. Each connection part is formed from the mountain of the annular part to the valley of the adjacent annular part, with the connection part oblique to the axis of the stent 50. The connection part is not disposed inside the annular part.

The mode of the annular part is not limited to those described above.

Figure 11:
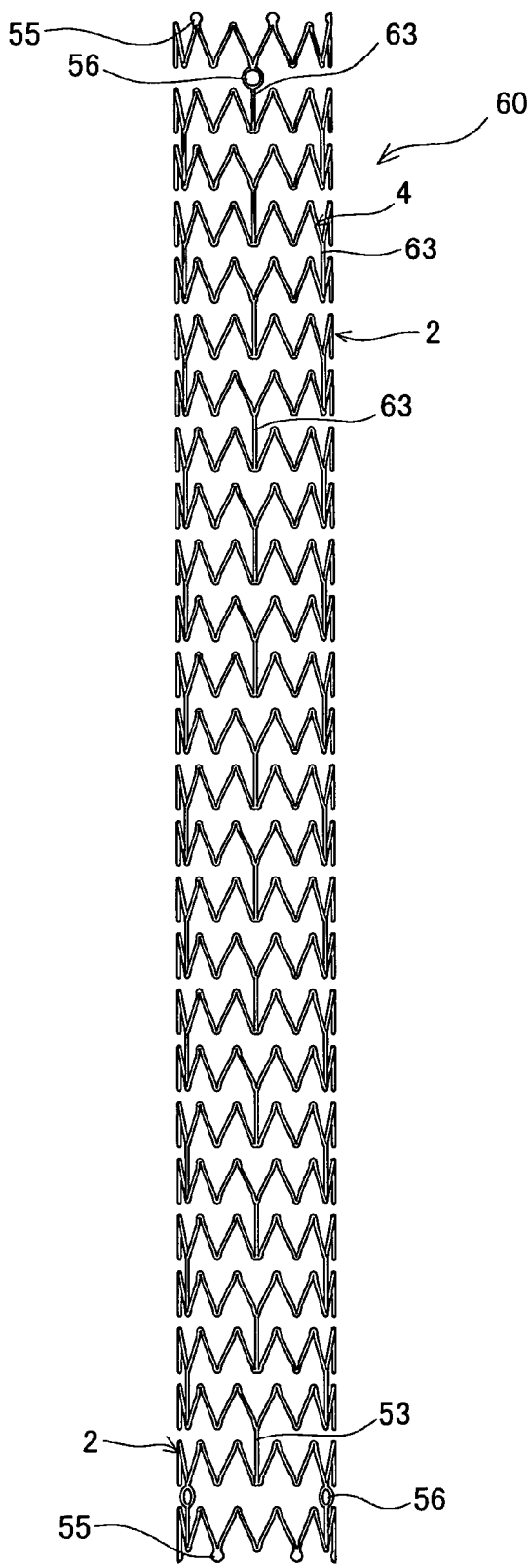
FIG. 11 is a front view showing a stent according to an embodiment of the present invention.
Figure 12:
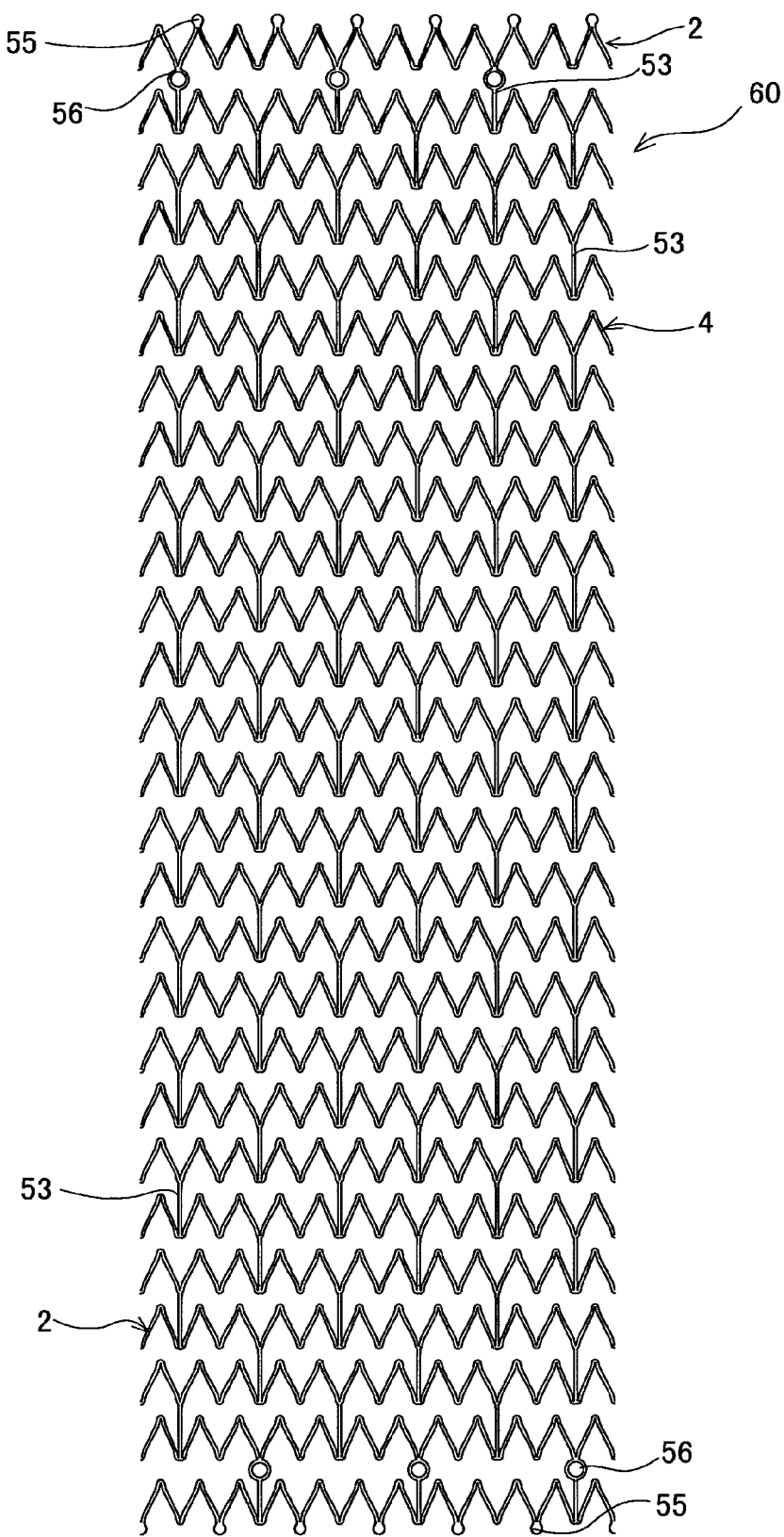
FIG. 12 is a development view showing the stent shown in FIG. 11.

FIG. 11 is a front view showing a stent according to an embodiment of the present invention. FIG. 12 is a development view showing the stent shown in FIG. 11. FIG. 13 is a partly enlarged view showing the stent shown in FIG. 11.

A stent 60 of this embodiment is almost the same as the above-described stent 50 except that the connection part 53 is substantially parallel with the axial direction (in other words, axis) of the stent 60. As shown in FIGS. 11 and 12, the stent 60 of the embodiment has a plurality of the annular parts 2 each composed of a linear material 4 that is wavy (zigzag) and annular and functions to keep the stent 60 expanded. The annular parts 2 are connected to one another with the connection parts 53 (connector) in such a way that the adjacent annular parts 2 do not separate from each other. A plurality of the annular parts 2 are arranged almost linearly in the axial direction of the stent 60, with mountains of the axially adjacent wavy annular parts 2 are almost straight. Similarly, plurality of the annular parts 2 are arranged almost linearly in the axial direction of the stent 60, with valleys of the axially adjacent wavy annular parts 2 are almost straight. That is, the modes and dispositions of the annular parts 2 are identical to each other. The connection part 53 is not substantially super-elastic entirely or partly and is plastically deformable. FIG. 13 is an enlarged view showing the neighborhood of the connection part 53 of the stent 60. The connection part 53 (portion shown with oblique lines) shown in FIG. 13 deforms plastically or normal elastically. When the stent 60 is bent, with the connection part 53 (portion shown with oblique lines) disposed radially outward, the connection part 53 deforms plastically. The occupation percentage of the plastically deformable portion (or normal elastically deformable portion) of the connection part 53 is favorably in the range of 10 to 100 and more favorably in the range of 40 to 100.

The connection part 53 of the stent 60 of the embodiment connects proximate valleys and valleys of the adjacent wavy annular parts 2 to each other. The connection part 53 is straight. The connection parts 53 are parallel with the axis of the stent 60.

In the stent 60 of the embodiment, the adjacent annular parts 2 are connected to each other by a plurality of the connection parts 53. It is preferable to connect the annular parts 2 to each other with a plurality of the connection parts 53. In the case where there are two connection parts 53, it is preferable to almost confront them at two positions of all the positions where the valleys and the mountains of the adjacent annular parts 2 confront each other. It is also preferable to dispose three or more connection parts 53, with the connection parts 53 forming an almost equal angle to the axis of the stent 60. In the embodiment, a plurality of valleys and mountains are formed on the axially adjacent wavy annular parts 2, with the valleys and the mountains proximate to each other. Valleys nearest to each other are connected to each other by the connection parts 53 every three valley. The connection parts 53 are parallel with each other. In the stent 60 of the embodiment, a part of the connection part 53 is disposed inside the annular part 2. The connection parts 53 are formed in such a way that they are uncontinuous in the axial direction of the stent 60. The connection parts 53 adjacent to each other in the axial direction of the stent 60 connect the valleys to each other alternately.

More specifically, in the stent 60 shown in FIGS. 11 and 12, the number of the zigzag lines of each annular part 2 is 12, and the connection part 53 is formed at three positions, with the connection parts 53 forming an equal angle to the axis of the stent 60. In the stent 60, a plurality of the annular parts 53 are formed, with the valleys adjacent to each other. The connection parts are parallel with the axis of the stent 60. Each connection part is formed from the valley of the annular part to the valley of the adjacent annular part, with a part of the connection part disposed between the adjacent annular part. By forming the stent 60 in the above-described configuration, it is possible to make the length of the connection part larger than that of the zigzag annular part and curve the stent easily at the connection part thereof.

Although the outer diameter of each of the stents 50 and 60 is different according to a portion where they are implanted, the outer diameter thereof is favorably in the range of 2.0 to 30 mm and more favorably in the range of 2.5 to 20 mm. The thickness of the stent is favorably in the range of 0.04 to 1.0 mm and more favorably in the range of 0.06 to 0.5 mm. The length of the stent is in the range of 10 to 150 mm and favorably in the range of 15 to 100 mm. In the case where the stent is implanted in a blood vessel, the outer diameter thereof is favorably in the range of 2.0 to 14 mm and more favorably in the range of 2.5 to 10 mm. The thickness of the stent is favorably in the range of 0.04 to 0.3 mm and more favorably in the range of 0.06 to 0.2 mm. The length of the stent is in the range of 5 to 80 mm and favorably in the range of 10 to 60 mm.

As described above, in the stents 50 and 60 of the embodiment, the annular part 2 is composed of a plurality of linear materials 4 wavy (zigzag) and annular. The number of waves is favorably in the range of 6 to 36 and more favorably in the range of 8 to 24. The length of the annular part 2 is favorably in the range of 1 to 10 mm and more favorably in the range of 1.5 to 5 mm. The number of the annular parts 2 is favorably in the range of 3 to 30 and more favorably in the range of 5 to 20. The distance between the adjacent annular parts 2 is favorably in the range of 2 to 7 mm. The length of the connection part 53 is favorably in the range of 2 to 10 mm. It is favorable that the width of the linear material 4 constituting the connection part 53 is small to allow the linear material 4 to be bent at a small force. More specifically, the width of the linear material 4 constituting the connection part 53 is favorably in the range of 0.03 to 0.2 mm and more favorably in the range of 0.05 to 0.12 mm.

As shown in FIGS. 8, 9, 11, and 12, in the stents 50 and 60 of the above-described embodiments, it is preferable that an apex 55 of the bent portion forming the outermost end of each of the annular parts 2 disposed at both ends of the stent has a bulged configuration to reduce a load to be applied by the outermost end of the stent to the inner wall of a lumen of the human body. It is preferable that as shown in FIGS. 8 and 11, both ends of the stent are approximately circular.

It is preferable to provide the stents 50 and 60 with a marker 56 made of an X-ray-unpermeable material. It is favorable to dispose the marker 56 at an end of the stent. It is more favorable to dispose the marker 56 at both ends of the stent. More specifically, as shown in FIGS. 8, 9, 11, and 12, it is preferable to dispose a plurality of the markers 56 at both ends of the stent. In the stents 50 and 60, the marker 56 is provided on the connection part 53 disposed at one extreme end thereof, and also at the other extreme end thereof.

The marker 56 made of the X-ray-unpermeable material is fixed to the stent with the marker 56 sealing a small opening formed on the stent. It is preferable to install the marker 56 on the small opening formed on the stent by disposing a disk-shaped member made of an X-ray contrast material a little smaller than the small opening and pressing and caulking both surfaces thereof. The form of the marker made of the X-ray-unpermeable material is not limited to the above-described type. For example, it is possible to apply the X-ray contrast material to the outer surface of the stent, wind a wire material formed of the X-ray contrast material around the stent or mount a ring-shaped member formed of the X-ray contrast material on the stent. It is preferable to form the marker 56 of gold, platinum, tungsten, tantalum, alloy thereof or silver-palladium alloy. The stents 1, 20, and 30 may be provided with the marker 56 made of the X-ray-unpermeable material.

A super-elastic alloy can be preferably used as the super-elastic metal forming the stent of each of the above-described embodiments. Herein the super-elastic alloy means a so-called shape memory alloy that shows super-elasticity essentially at the temperature (in the vicinity of 37° C.) of the human body. The following super-elastic metals can be preferably used: A Ti—Ni alloy of 49 to 53 atomic percent of Ni, a Cu—Zn alloy of 38.5 to 41.5 wt % of Zn, a Cu—Zn—X alloy of 1 to 10 wt % of X (X=Be, Si, Sn, Al, Ga), and a Ni—Al alloy of 36 to 38 atomic percent of Al. The Ti—Ni alloy is most favorable. The mechanical characteristic of the Ti—Ni alloy can be appropriately changed by replacing a part of the Ti—Ni alloy with 0.01 to 10.0% of X to obtain a Ti—Ni—X alloy (X=Co, Fe, Mn, Cr, V, Al, Nb, W, B) or by replacing a part of the Ti—Ni alloy with 0.01 to 30.0 atomic percent of X to obtain a Ti—Ni—X alloy (X=Cu, Pb, Zr). Further the mechanical characteristic of the Ti—Ni alloy can be appropriately changed by selectively adopting a cold working ratio or/and the condition of final heat treatment. In the case where the Ti—Ni—X alloy is used, it is also possible to change its mechanical characteristic appropriately by selectively adopting a cold working ratio or/and the condition of final heat treatment.

The buckling strength (yield stress when load is applied to stent) of the super-elastic alloy to be used is favorably in the range of 5 to 200 kg/mm$^2$ (22° C.) and more favorably in the range of 8 to 150 kg/mm$^2$. The restoring stress (yield stress when load is eliminated from stent) of the super-elastic alloy is favorably in the range of 3 to 180 kg/mm$^2$ (22° C.) and more favorably in the range of 5 to 130 kg/mm$^2$. The super-elasticity means that when a metal is deformed (bent, stretched, compressed) to a region in which it deforms plastically at a service temperature, it returns to its original configuration without heating it after the deformation is released.

The stent is formed by removing (for example, cutting, dissolving) a part, of a pipe made of a super-elastic metal, not constituting the stent. Thereby the stent is obtained as an integral product.

The pipe made of the super-elastic metal to be used to form the stent of the present invention can be produced by dissolving a super-elastic alloy such as the Ti—Ni alloy in an inactive gas atmosphere or a vacuum atmosphere to form an ingot thereof, polishing the ingot mechanically, forming a pipe having a large diameter by hot press and extrusion, repeating drawing step and heat treatment step to adjust the diameter and thickness of the pipe to a predetermined thickness and reduced diameter, and finally polishing the surface of the pipe chemically or physically.

The pipe made of the super-elastic metal can be processed into the base material for the stent by a cutting work such as laser processing (for example, YAG laser), electrical discharge machining, and the like or chemical etching or in combination thereof.

The stent of the present invention may be coated with a material suitable for the human body on its inner surface, outer surface or inner and outer surfaces. As the material suitable for the human body, synthetic resin and metal suitable for the human body can be used. The following inactive metals are used to coat the surface of the stent: gold by electroplating method, stainless steel by evaporation method, silicon carbide by sputtering method, plated titanium nitride by sputtering method, and plated gold by sputtering method.

As the synthetic resin, the following thermoplastic resins or thermosetting resins can be used: polyolefin (for example, polyethylene, polypropylene, ethylene-propylene copolymer), polyvinyl chloride, ethylene-vinyl acetate copolymer, polyamide elastomer, polyurethane, polyester, fluorocarbon resin, silicone rubber. Polyolefin, polyamide elastomer, polyester, and polyurethane are favorable. A resin decomposable in the human body (polylactic acid, polyglycolic acid, polylactic acid-polyglycolic acid copolymer) is also favorable. It is preferable that the film of the synthetic resin is soft to such an extent as not to prevent frames constituting the stent from being curved. The thickness of the film of the synthetic resin is favorably in the range of 5 to 300 μm and more favorably in the range of 10 to 200 μm.

As the method of thinly coating the surface of the stent with the synthetic resin, it is possible to use a method of inserting the pipe made of the super-elastic metal into the melted synthetic resin or into the synthetic resin dissolved in a solution. It is also possible to use a chemical evaporation method of polymerizing a monomer on the surface of the pipe made of the super-elastic metal. In the case where the surface of the stent is coated very thinly with the synthetic resin, the use of a dilute solution or chemical evaporation method is preferable.

To improve the quality of the material suitable for the human body to a higher extent, the resinous film may be coated with an anti-thrombus material or the anti-thrombus material may be fixed to the resinous film. As the anti-thrombus material, known various resins can be used singly or as a mixture thereof. For example, polyhydroxyethyl methacrylate, copolymer of hydroxyethyl-methacrylate and styrene (for example, HEMA-St-HEMA block copolymer) can be preferably used.

The method of producing the stent of the present invention is described below.

There is provided a method of producing a stent to be implanted in a human body, including the steps of forming a base material for the stent having a plurality of annular parts deformable in a direction in which an outer diameter thereof contracts, when a stress is applied thereto and a plurality of connection parts each connecting the adjacent annular parts to each other, with the annular parts arranged in an axial direction of the stent by partly removing a side surface of a prepared approximately cylindrical pipe, made of a super-elastic metal, having an outer diameter suitable for a portion of the human body in which the stent is implanted; and heat-treating a part or an entirety of the connection part of the base material for the stent to substantially eliminate super-elasticity of each of the connection parts and impart plastic deformability or normal elasticity thereto.

The pipe made of the super-elastic metal can be produced by dissolving a super-elastic alloy such as the Ti—Ni alloy in an inactive gas atmosphere or a vacuum atmosphere to form an ingot thereof, polishing the ingot mechanically, forming a pipe having a large diameter by hot press and extrusion, repeating drawing step and heat treatment step to obtain a predetermined reduced thickness and diameter of a semi-finished product of the stent, and finally polishing the surface thereof chemically or physically.

A cutting work such as laser beam machining (for example, YAG laser), electrical discharge machining, and mechanical polishing or chemical etching can be used or in combination thereof to perform the step of forming a base material for the stent having a plurality of annular parts deformable in a direction in which an outer diameter thereof contracts, when a stress is applied thereto and a plurality of connection parts each connecting the adjacent annular parts to each other, with the annular parts arranged in an axial direction of the stent by partly removing a side surface of a prepared approximately cylindrical pipe, made of a super-elastic metal. Since the stent is formed by processing the pipe as described above, the outer diameter of the processed pipe is equal to that of the stent. Thus the stent formed in this manner has high dimensional accuracy and returns to its original configuration when it is implanted in the human body. Therefore it is possible to securely improve a stenosed portion of the human body.

More specifically, in the step of forming the base material for the stent, a primary processing step of initially processing the base material for the stent into a predetermined configuration is carried out. That is, initially electrical discharge machining is conducted to fuse the portion, of the pipe made of the super-elastic metal, not constituting the base material for the stent. Thereby the portion of the pipe not constituting the base material for the stent is removed. Thereafter a chamfering step (secondary processing) of shaving the edge of the primarily processed pipe for the stent is carried out. In the chamfering step, blast treatment is conducted for removal of a burr and chamfering by using hard fine particles. In the case where a thermally modified portion is formed on the peripheral edge of the primarily processed pipe, a step of treating the thermally modified portion (tertiary step, chemical etching) may be conducted to remove the thermally modified portion. The step of treating the thermally modified portion is performed by immersing the primarily processed pipe that has undergone the blast treatment in a thermally modified portion-treating solution in which a mixture of hydrofluoric acid and nitric acid is mixed with a small amount of hydrogen peroxide solution. The chemical etching (thermally modified portion-treating step) may be used to accomplish burr removal and chamfering simultaneously. In this case, it is unnecessary to carry out the blast treating step.

It is preferable that in the primary processing of the step of forming the base material for the stent from the pipe made of the super-elastic metal, the prepared pipe, made of the super-elastic metal, having a predetermined outer diameter is machined by using a laser apparatus (for example, YAG laser apparatus).

The step of forming the base material for the stent from the pipe made of the super-elastic metal may be performed by using photo-fabrication technique, as described below.

In this method, initially, grease is removed from the inner and outer surfaces of the pipe made of the super-elastic metal. Then they are cleaned. The grease removal and cleaning are conducted by immersing the pipe in a solution containing a surface-active agent, immersing the pipe in an RO solution or immersing the pipe in a cleaning organic solvent of hexane or the like. After the pipe is dried, a photo-resist is applied to the inner and outer surfaces of the pipe. As the photo-resist, both positive type and negative type can be used. A UV resist, an electron beam resist, and an X-ray resist may be used. The thickness of the photo-resist is preferably in the range of 0.5 to 4 μm. To enhance the adhesiveness of the photo-resist film to the pipe, heat treatment (pre-baking) is performed at 80 to 90° C.

Thereafter a masking film (different according to whether photo-resist is of positive type or negative type) having a pattern corresponding to the predetermined configuration of the base material for the stent is wound around the outer surface of the pipe made of the super-elastic metal to bring the masking film into close contact with the outer surface of the pipe in a vacuum atmosphere. Then an exposing work is performed. The exposing work can be performed by using a super-high pressure mercury vapor lamp. It is preferable to perform the exposing work by rotating the pipe so that the pipe is entirely and securely irradiated. Then developing treatment is performed. The developing treatment is performed by immersing the pipe in a photo-resist developer. Thereafter the developer is heated to 120 to 145° C. to perform post-baking treatment. Thereby the masking process terminates.

In the pipe processed as described above, the photo-resist is not present in the portion of the pipe not constituting the base material for the stent, whereas the hardened photo-resist is present in the portion of the pipe constituting the base material for the stent. The semi-finished product for the stent is immersed in an etching solution to dissolve the portion of the pipe not constituting the base material for the stent therein. Thereby the portion of the pipe not constituting the base material for the stent is removed. The portion of the pipe not constituting the base material for the stent is dissolved in the etching solution because it contacts the etching solution. On the other hand, the hardened photo-resist prevents the portion of the pipe constituting the base material for the stent from contacting the etching solution. Therefore the portion of the pipe constituting the base material for the stent is not dissolved in the etching solution. The base material for the stent having an outer configuration similar to that of the stent is formed by the treatment conducted by using the etching solution. Thereafter the hardened photo-resist that has attached to the surface of the base material for the stent is removed. This treatment is performed by immersing the base material for the stent in a solution in which the hardened photo-resist dissolves. Further, to remove the burr formed on the peripheral edge of the base material for the stent and chamfer it, the blast treatment is carried out, as described above. Then the base material for the stent is immersed in the etching solution to perform surface treatment. Thereby the base material for the stent is formed.

As necessary, the step of plating the semi-finished product for the stent with metal or forming a resinous film thereon is performed. The semi-finished product for the stent is plated with gold by electroplating method, stainless steel by evaporation method, silicon carbide by sputtering method, titanium nitride or gold.

It is favorable that the configuration of the base material for the stent formed as described above is the same as that of any of the stents 1, 20, 30, 50, and 60. It is most favorable that the configuration of the base material for the stent is the same as that of the stent 1. However, the configuration of the base material for the stent is not limited to that of the stents 1, 20, 30, 50, and 60.

Thereafter heat treatment step is performed. The connection part of the base material for the stent is heated to substantially eliminate the super-elasticity of the connection part and impart plastic deformability thereto.

The step of heat-treating the connection part is executed by a heat developed by an electric resistance of each connection part that is energized at both ends thereof (electric resistance method), irradiating each connection part with a laser beam (laser heating method) or pressing a highly heated tool such as a soldering iron against each connection part (direct heating method).

In the case where the electric resistance method is used, a high-voltage electricity is applied to only both ends of the connection part to heat the connection part by the electric resistance of the super-elastic metal. This method is capable of easily controlling heating because the connection part can be heated to a high temperature by an instantaneous energization of both ends thereof and because the connection part is cooled rapidly by terminating the energization. When this method is used, it is efficient that the connection part is comparatively long because the resistance of the super-elastic metal is high.

In performing the laser heating method, it is preferable to use YAG laser and semiconductor excitation laser as the laser. It is possible to adjust heating energy by adjusting the output and focal distance thereof.

In using the direct heating method, it is preferable to use a soldering iron having a length equal to or longer than the connection part.

In any of the above-described methods, it is preferable to use the base material for the stent in which the connection part is disposed in an annular portion (between adjacent annular parts) orthogonal to the axis of the base material for the stent. By using the base material for the stent in this mode, the heat treatment process can be performed easily. More specifically, by intermittently rotating the base material for the stent fixed to an apparatus, heat treatment of the connection part disposed in one annular portion can be accomplished. After the treatment of the connection part in one annular portion terminates, the base material for the stent or the base material to be heated is moved axially to sequentially perform heat treatment of the connection parts in other annular portions.

When the base material for the stent is stopped during its intermittent rotation, the following operations are performed in each heat treatment method: energizing contacts are brought into contact with the connection part to heat it when the electric resistance method is used; laser beams are emitted to each connection part when the laser heating method is used; and the connection part is allowed to contact a heat source when the direct heating method is used.

Although the heating temperature in the heat treatment for the connection part is different according to the metallic composition of the super-elastic alloy and a temperature treatment condition for imparting the super-elasticity thereto, the heating temperature at a portion of the connection part where an elastic deformation is eliminated favorably in the range of 400 to 600° C. and more favorably in the range of 450 to 550° C.

It is preferable that the step of heat-treating (heat treatment step) is performed by disposing a base material for a stent on a heat sink on which the base material for the stent can be mounted and which has a plurality of concavities, with each annular part of the base material for the stent in contact with an outer surface of the heat sink and with the connection part, an entirety of a portion thereof or a portion thereof over the concavities of the heat sink, namely, not in contact with the outer surface of the heat sink and by energizing the entire base material for the stent so that the base material for the stent self-heats and the annular part in contact with the outer surface of the heat sink radiates heat.

This heat treatment step is the same as that of the method, which will be described later, of producing the stent to be implanted in the human body. Thus the description of the heat treatment step is omitted herein.

It is preferable that the method, of the present invention, of producing the stent to be implanted in the human body is as follows:

The method of producing the stent to be implanted in the human body comprises the steps of forming a base material for the stent having a plurality of annular parts and a plurality of connection parts each connecting the adjacent annular parts to each other, with the annular parts arranged in an axial direction of the stent by preparing an approximately cylindrical metal pipe having an outer diameter smaller than an inner diameter of a portion in which the stent is implanted and having super-elasticity or a shape memory characteristic or to which the super-elasticity or the shape memory characteristic can be imparted and by partly removing a side surface of the pipe; forming an expanded mode of the base material for the stent by expanding the base material for the stent so that an outer diameter thereof becomes suitable for the portion in which the stent is implanted and by heat-setting (heat-treating) the base material for the stent in an expanded state to store a configuration of the expanded base material for the stent and allow the super-elasticity to appear; and heat-treating the expanded base material for the stent by heating an entirety or a portion of the connection parts to eliminate super-elasticity thereof substantially and impart plastic deformability or normal elasticity thereto.

Each step will be described below.

Initially the step of forming the base material for the stent is carried out.

Prepared in the above step may be an approximately cylindrical metal pipe which has an outer diameter smaller than an inner diameter of a portion of the human body in which the stent is implanted and to which super-elasticity or a shape memory characteristic can be imparted.

The metal to be prepared may have the super-elasticity or the shape memory characteristic. Otherwise, the super-elasticity or the shape memory characteristic may be imparted to a metal pipe in a processing step which will be described later.

The pipe can be produced by dissolving a super-elasticity-impartable alloy such as an Ti—Ni alloy in an inactive gas atmosphere or a vacuum atmosphere to form an ingot thereof, polishing the ingot mechanically, forming a pipe having a large diameter by hot press and extrusion, repeating drawing step and heat treatment step to adjust the diameter and thickness of the pipe to a predetermined thickness and reduced diameter, and finally polishing the surface of the pipe chemically or physically.

The side surface of the pipe is partly removed to form the base material for the stent having a plurality of annular parts and a plurality of connection parts each connecting the adjacent annular parts to each other, with the annular parts arranged in an axial direction of the stent. This step can be accomplished by a cutting work such as laser processing (for example, YAG laser), electrical discharge machining, mechanical polishing or chemical etching or in combination thereof.

Thereafter the step of forming an expanded mode of the base material for the stent is performed by expanding the outer diameter of the base material for the stent prepared as described above so that the diameter is suitable for a portion of the human body in which it is implanted and by performing heat-setting in a base material-expanded state to store the configuration of the base material for the stent in the base material-expanded state and allow the super-elasticity to appear.

The step of expanding the outer diameter of the base material for the stent prepared as described above so that the diameter is suitable for a portion of the human body in which it is implanted can be accomplished by using a mandrel having a tapered portion having a smaller diameter than that of the base material for the stent at its one end thereof so that the one end thereof can be inserted into the base material for the stent. The mandrel has a large-diameter portion continuous with the tapered portion, whose diameter is equal to the outer diameter of the stent in the expanded state. The end of the tapered portion of the mandrel is inserted into the base material for the stent, and the base material for the stent is pressed into the large-diameter portion of the mandrel. Thereby the base material for the stent is expanded. The step of expanding the stent base material may be performed stepwise. More specifically, a plurality of mandrels different in the length of the outer diameter of the large-diameter portion are prepared. The above-described expanding step (primary expansion) is performed by using the mandrel having a small outer diameter. Then an expanding step (secondary expansion) is performed by using the mandrel having a large outer diameter. As necessary, an expanding step (tertiary expansion) is performed by using the mandrel having a larger outer diameter In the step of heat-setting the base material for the stent in an expanded state to store the configuration of the base material for the stent in the expanded state and allow the super-elasticity to appear, the base material for the stent is heated by a heating means such as a heater, with the base material for the stent disposed on the large-diameter portion of the mandrel to store the configuration of the expanded base material for the stent and impart the super-elasticity thereto. That is, by heating the base material for the stent fitted on the mandrel, heat treatment is performed in such a way that a stored configuration of the stent is the outer diameter of the large-diameter portion of the mandrel. It is preferable to heat-treat the base material for the stent in an atmosphere of an inactive gas such as argon, nitrogen or the like. Air can be also used as the atmosphere for the heat treatment thereof.

The heating temperature and the heating time period at this step (heat-setting step) is different according to a metal to be used. It is preferable to heat the base material for the stent at 350 to 550° C. for five to twenty minutes.

After the base material for the stent is cooled, it is removed from the mandrel. It is preferable to air-cool it. More specifically, it is preferable to cool it rapidly. The entire base material for the stent, containing the connection part, obtained at this step has the super-elasticity (or shape memory characteristic).

Thereafter the entirety or a portion of the connection parts expanded and having the super-elasticity is heated to substantially eliminate the super-elasticity thereof and impart plastic deformability or normal elasticity thereto.

The heat treatment is performed by disposing a base material 100 for the stent on a heat sink 80 on which the expanded base material 100 for the stent can be mounted and which has a plurality of concavities 81, with each annular part 2 of the base material 100 for the stent in contact with an outer surface of the heat sink 80 and with connection parts 53, an entirety of a portion thereof or a portion thereof disposed over the concavities 81 of the heat sink and not in contact with the outer surface of the heat sink and by energizing the entire base material 100 for the stent so that the base material 100 for the stent self-heats and the annular part in contact with the outer surface of the heat sink 80 radiates heat.

Figure 14:
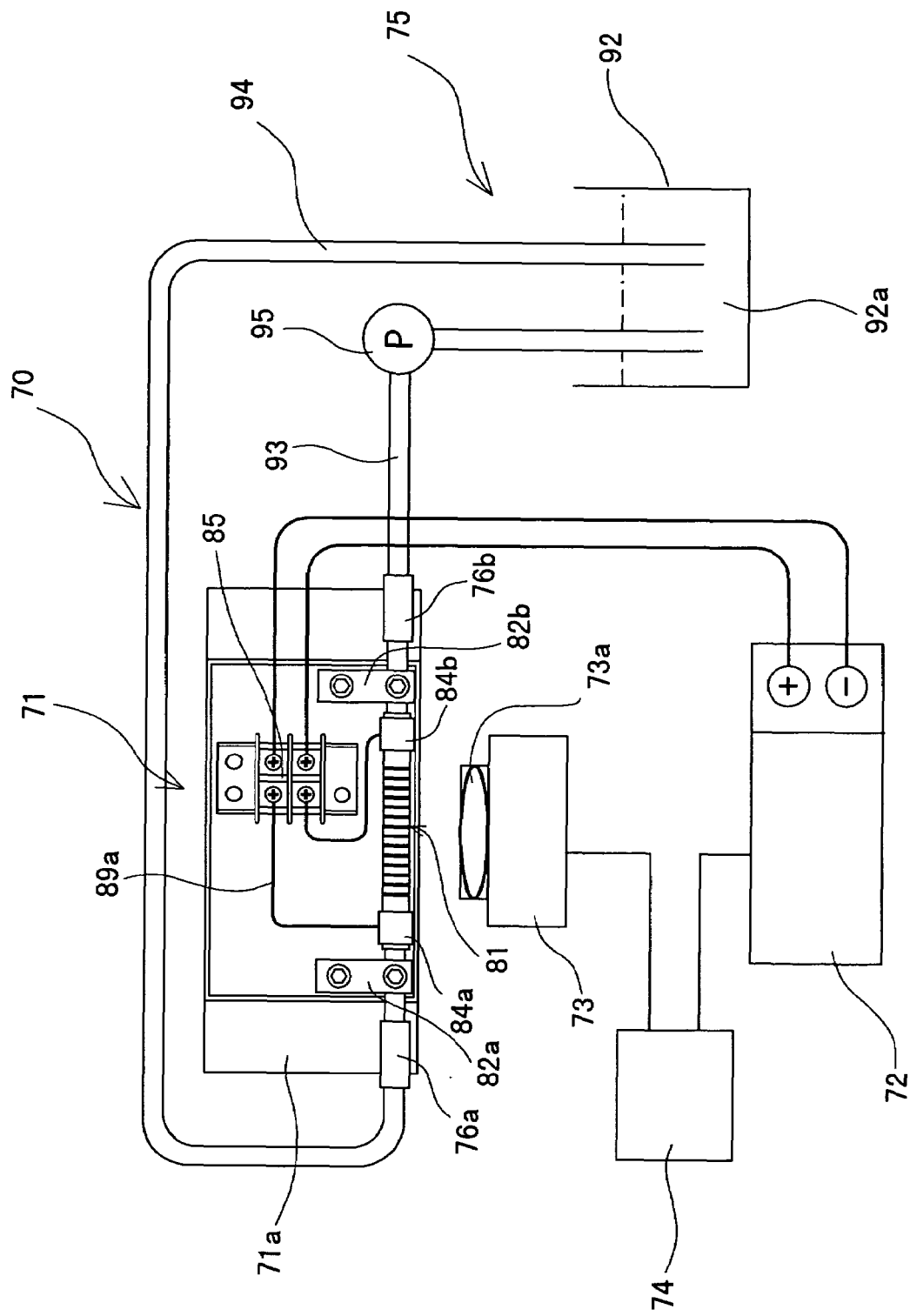
FIG. 14 is an explanatory view for explaining an example of a heat treatment apparatus to be used in a heat treatment step.

FIG. 14 is an explanatory view for explaining an example of a heat treatment apparatus to be used in the heat treatment step.

A heat treatment apparatus 70 has a stent-heating device 71, a power supply device 72 for supplying electric current to the stent-heating device 71, a heated state grasping device 73 for grasping the heated state of the stent, a controller 74 for controlling the operation of the power supply device 72 by using information of the heated state grasped by the heated state grasping device 73, and a cooling device 75 for cooling the heat-treated stent.

The stent-heating device 71 has a heat sink 80 on which the stent to be heat-treated is mounted, heat sink gripping portions 82a, 82b, electrodes 84a, 84b for energizing the stent, and a connection terminal 85 for connecting the electrodes 84a, 84b to the power supply device 72.

Figure 15:
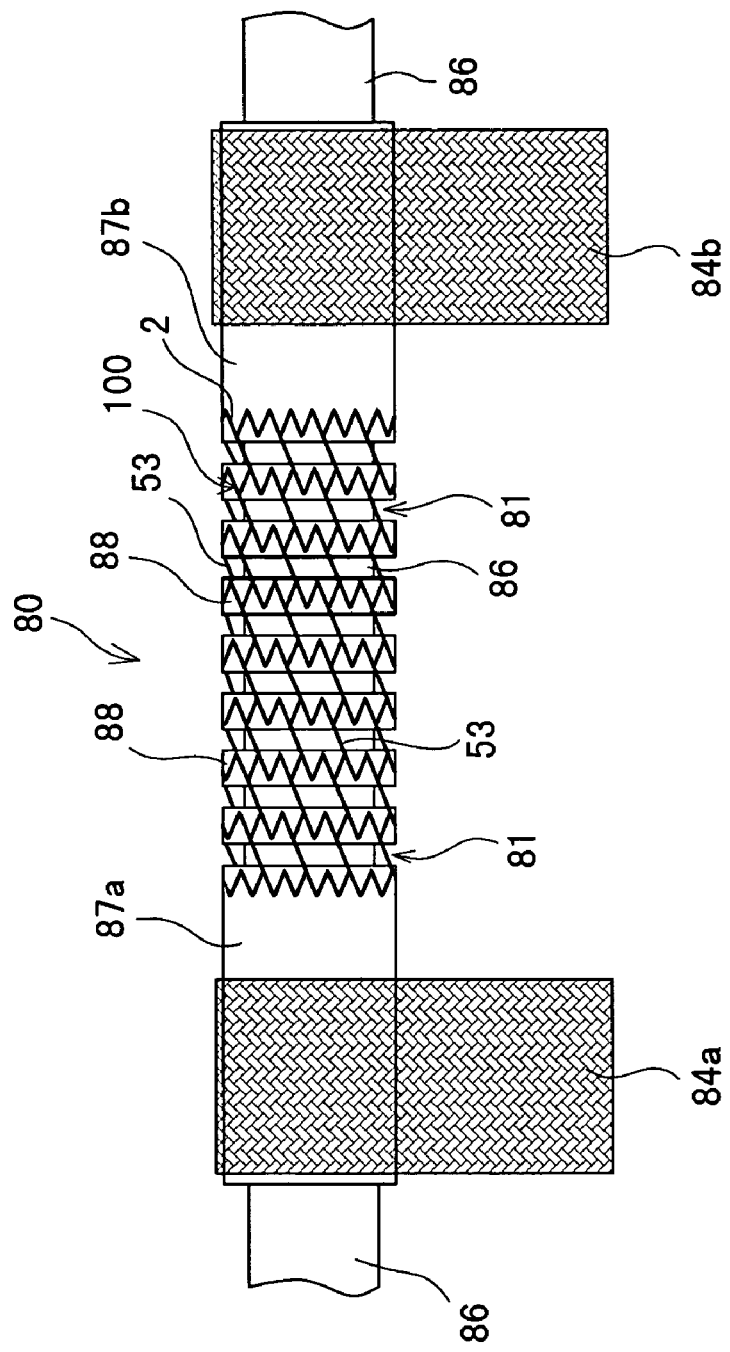
FIG. 15 shows a heat sink of the heat treatment apparatus shown in FIG. 14.

As shown in FIG. 15, the base material for the stent in the expanded mode can be mounted on the heat sink 80. The heat sink 80 has a plurality of concavities 81. More specifically, the heat sink 80 has a base shaft 86 whose surface has been insulated, electrode-mounting cylinders 87a, 87b made of a conductive material and fixed to the base shaft 86, with a predetermined interval spaced between each other, a plurality of ring-shaped member 88 made of a conductive material and disposed between the electrode-mounting cylinders 87a and

87b in such a way that the ring-shaped members 88 do not contact each other. The concavities 81 are formed between the ring-shaped members 88 and the electrode-mounting cylinders 87a as well as 87b. As the base shaft 86, a metal pipe having preferable heat transfer property and a insulated outer surface is used in the embodiment. A cooling liquid circulated by the cooling device flows through the pipe. As the base shaft 86, an aluminum pipe whose surface has been insulated is preferable. As the method of insulating the base shaft 86, it is preferable to form an insulating film thereon. As the insulating film, the following resins are suitable: fluorocarbon resin such as PTFE and ETFE; and thermosetting resins such as epoxy resin, silicone resin, phenol resin, polyimide resin, melamine resin, and urea resin. The thickness of the film coating the surface of the base shaft 86 is favorably in the range of 20 μm to 50 μm. In the case where the aluminum pipe is used as the base shaft 86, it is preferable to insulate its surface with anodized aluminum. In this case, the thickness of the anodized aluminum is favorably in the range of 15 μm to 50 μm.

It is preferable that the electrode-mounting cylinders 87a, 87b and the ring-shaped member 88 are made of metal such as copper and brass.

The cooling device 75 has a cooling liquid tank 92, ducts 93, 94, a pump 95, and connectors 76a, 76b connected to the base shaft 86. A cooling liquid 92a inside the cooling liquid tank 92 is circulated by the pump 95 through the duct 93, the connectors 76b, the base shaft 86, the connector 76a, the duct 94, and returned to the cooling liquid tank 92. As the cooling liquid, water, polyethylene glycol and the like are used. It is unnecessary to provide the cooling liquid tank 92 with a cooling means because heat is radiated naturally when the cooling liquid tank 92 contains a large amount of cooling liquid. In the case where a small amount of cooling liquid is used, it is preferable to provide the cooling liquid tank 92 with a cooling means such as a chiller for cooling the cooling liquid.

The cooling device does not necessarily have to be provided with the cooling liquid, but may be provided with a cooling module. In the case where the cooling module is used, it is installed on the base shaft. In this case, it is preferable that the base shaft is solid. As the cooling module, it is possible to use a thermo module using a Peltier element, an electronic cooling module, and the like.

As shown in FIG. 15, in the embodiment, each annular part 2 of the base material for the stent 100 contacts the outer surface of the heat sink 80, and all of the connection parts 53 other than both-end of the connection parts 53 are disposed over the concavities 81 so that they do not contact the outer surface of the heat sink 80.

As shown in FIGS. 14 and 15, the electrodes 84a, 84b are mounted on the electrode-mounting cylinders 87a, 87b of the heat sink 80. As shown in FIG. 14, both ends of the base shaft 86 are gripped by the heat sink gripping portion 82a, 82b and fixed to a base 71a. The electrodes 84a, 84b are connected to the connection terminal 85 through lead wires 89a, 89b. It is preferable that the electrodes 84a, 84b are reticulate, as shown in FIG. 15.

As the power supply device 72, a DC power supply device is used. As the power supply device, a constant-current regulated power is preferable. The power supply device 72 is connected to the connection terminal 85 through lead wires 72a, 72b. The electrodes 84a, 84b may be connected directly to the power supply device 72 without providing the connection terminal.

As the heated state grasping device 73 for grasping the heated state of the stent, a non-contact type such as a thermography apparatus and a spot thermometer is used. When the thermography apparatus is used, a lens 73a for observing the stent enlargingly is provided. The thermography apparatus 73 grasps the heated situation of the stent while it is heated and sends the information thereof to the controller 74.

As the controller, a personal computer is used. The controller 74 is connected to the power supply device directly or indirectly. The controller 74 has a function of controlling the operation of the power supply device. More specifically, the controller 74 controls on and off of the power supply device or electric current or a voltage so that the thermography apparatus 73 grasps the heated state of the connection part of the stent which is heated to a desired temperature.

The base material 100 for the stent is disposed on the heat sink 80 of the heat treatment apparatus having the above-described construction, with each annular part 2 of the base material 100 for the stent in contact with the outer surface of the heat sink 80 and with at least the central portion of each connection part 2 disposed over the concavities 81 of the heat sink 80 and not in contact with the outer surface of the heat sink. The controller 74 is operated to flow direct current between the electrodes 84a and 84b from the power supply device to thereby self-heat the base material 100 for the stent. Further the cooling device is operated to cool the base shaft and the heat sink 80. Thereby a self-heated portion of the base material 100 for the stent in contact with the heat sink 80 is cooled, whereas the connection part not in contact with the heat sink 80 remain self-heated. A portion of the connection part not in contact with the heat sink 80 but proximate thereto is a little cooled and thus has a lower temperature than that of the central portion thereof.

More specifically, with reference to FIG. 14, electric current supplied from the power supply device 72 flows through the electrode 82b, the electrode-mounting cylinder 87b, the right end of the base material for the stent, the left end of the base material for the stent, the electrode-mounting cylinder 87a, the electrode 82a, and the power supply device 72. As shown in FIG. 16, because the ring-shaped members 88 of the heat sink 80 and the base shaft 86 are insulated from each other, the electric current flows through the base material 100 for the stent collectively. Upon application of the electric current to the base material 100 for the stent, the base material 100 for the stent generates Joule heat. Since the annular part 2 and a part of the connection part 53 contact the heat sink 80 (namely, ring-shaped members 88), the heat escapes to the heat sink 80 (namely, ring-shaped members 88). Thus the temperature of the stent does not rise. Because the portion (central portion) of the connection part 53 corresponds to the groove of the heat sink 80, the Joule heat generated in the central portion of the connection part 53 does not escape to the heat sink. Thus the central portion of the connection part 53 self-heats. The self-heating temperature can be controlled by an amount of electric current flowing through the base material 100 for the stent.

More specifically, data measured by the thermography (non-contact type thermometer) is inputted to the personal computer serving as the controller through a communication means such as a GPIB or an RS-232C. The personal computer performs an appropriate computation on measured data, based on the difference between a predetermined target temperature and a measured temperature. The result of the computation (data obtained by computation) is inputted to the DC power supply device through the communication means. Output electric current of the DC power supply device is controlled so that the temperature of the connection part has the target temperature. In this manner, based on the program stored by the personal computer, the temperature of the connection part can be maintained at a desired temperature for a desired period of time.

According to this method, a plurality of stents having the same configuration (designs, lengths, diameters are equal to each other) can be heat-treated easily and simultaneously.

To this end, a plurality of annealing jigs are disposed, with stents set thereon, and they are wired in such a way that heating electric current are connected in series. The cooling device (cooling liquid tank can be used commonly) and cooling liquid pipes are arranged in parallel for each annealing jig. This method allows electric current/voltage having the same value to be applied to the stents and allows heat to escape to the heat sink in the same manner. Therefore it is possible to heat-treat a plurality of stents at the same time and in the same manner. In this case, regarding the temperature of the connection part, monitoring (measuring) of any one of the stents is sufficient.

Figure 17:
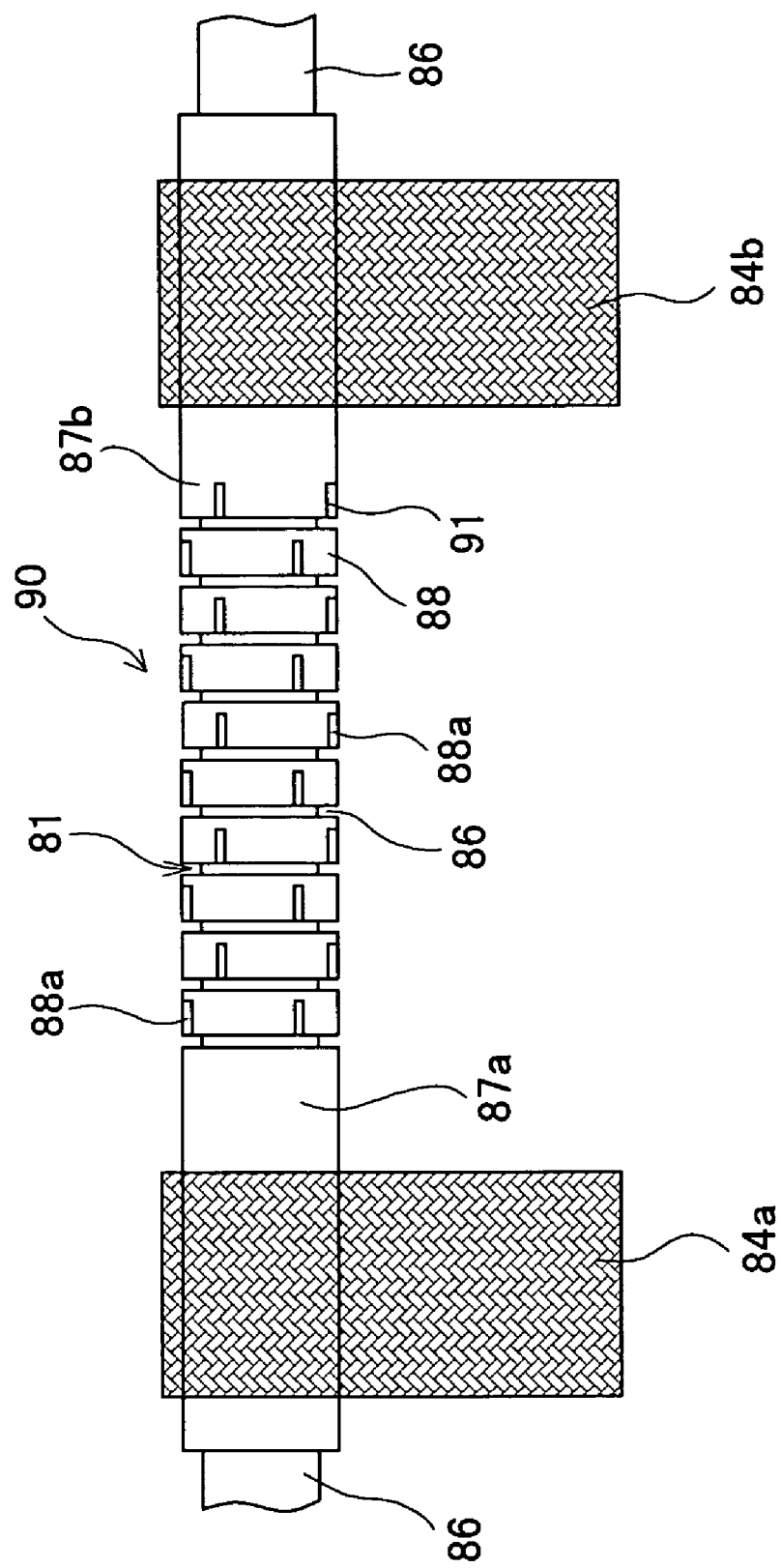
FIG. 17 shows a heat sink according to another embodiment.

A heat sink 90 having a mode shown in FIG. 17 is used for the stent 60, shown in FIGS. 11 through 13, in which a portion of the connection part 53 is disposed inside the annular part 2. The heat sink 90 is different from the above-described heat sink in that the ring-shaped member and the electrode-mounting cylinder are provided with a groove for preventing contact between them and the connection part. In particular, in the heat sink 90, a plurality of grooves 88*a* are formed on the outer surface of the ring-shaped member 88, and a plurality of grooves 91 are formed on the electrode-mounting cylinder 87*b*. The width of each of the grooves 88*a* and 91 is set larger than that of the connection part.

It is possible to heat-treat the central portion of the connection part and plasticize and soften it with the annular part 2 and both ends of the connection part 53 maintaining super-elasticity. Although the percentage of the length of the connection part to be plasticized depends on the design of the stent, it is favorably in the range of 10% to 100% and more favorably in the range of 40%-90%.

The examples of the present invention are described below.

EXAMPLE 1

Cold working of a Ti—Ni alloy (51 atomic percent of Ni) was performed to prepare a super-elastic metal pipe having an outer diameter of about 8 mm, an inner diameter of about 7.6 mm, and a length of about 34 mm. The super-elastic metal pipe was set on a jig provided with a rotary motor having a fastening mechanism in such a way as to prevent the pipe from being off-centered. Thereafter the jig was set on an XY table capable of making a numerical control. The XY table and the rotary motor were connected to a personal computer. An output of the personal computer was inputted to a numerical controller of the XY table and the rotary motor. A development drawing representing the stent having the structure shown in FIG. 2 was inputted to the personal computer storing a design software.

The XY table and the rotary motor were driven in accordance with design data outputted from the personal computer. The pipe was irradiated with a laser beam to machine the pipe into a base material for the stent having the configuration shown in FIG. 1.

As the laser machining condition for the metal pipe, current value was set to 25 A, an output was set to 1.5 W, and a drive speed was set to 10 mm/min. It is not limited to above-described system as a laser marker. It may be a so-called laser marker(Galvanometer system) the laser processing machine of which drives.

The base material for the stent was dipped in a heated chemical polishing solution for about two minutes to chamfer (removal of burr and chemical polishing) it.

Thereafter energizing contacts were brought into contact with each connection part to apply direct current thereto. Thereby the portion between both the energizing contacts generated heat at about 490 degrees for several seconds.

The stent prepared in this manner had an outer diameter of about 8 mm, an entire length of 34 mm, and a thickness of 0.2 mm. The width of the linear material constituting the annular part (expansion element) was 0.12 mm. The connection part (connector element) had a width of 0.06 mm. The entire connection part was plastically deformable.

EXAMPLE 2

The entire surface of the stent of the example 1 was gold plated. The stent of the example 1 was immersed in a sulfamic acid plating bath (produced by Tokuriki Kabushiki Kaisha, trade name: Auroflex T1) heated at 40° C. Potassium cyanide was dissolved in the plating bath. Thereby an unglossy gold-plated layer having a thickness of 1.8 μm was formed on the surface of the stent.

COMPARISON EXAMPLE

A stent entirely showing super-elasticity having the following size was obtained by carrying out a method similar to that of the example 1 except that connection part was not heat-treated. The stent had an outer diameter of about 8 mm, an entire length of 34 mm, and a thickness of 0.2 mm. The width of the linear material constituting the annular part (expansion element) was 0.12 mm. The connection part (connector element) had a width of 0.06 mm.

EXPERIMENT

The stent of the example 1 and that of the comparison example were wound around a rod having a diameter of 50 mm. Then an operator's hand was released from the stents and the deformed state of the stents was observed. The result was that the stent of the comparison example was not deformed and had an original configuration, whereas the stent of the example 1 was curved gently at a radius of curvature of about 35 mm. This indicates that the stents of the examples deform for a load applied thereto.

EXAMPLE 3

A super-elastic (or shape memory) Ti—Ni alloy pipe (for example, outer diameter was about 1.6 mm, thickness was about 0.2 mm, and length was 1 m) was cut by laser beams to obtain a base material for the stent. More specifically, the pipe was set on an Xθ table whose movement was controlled by a computer to which a development drawing of the stent shown in FIG. 9 was inputted. The outer surface of the pipe was convergently and intermittently irradiated by laser beams. Thereby the base material for the stent having a small diameter was prepared.

Thereafter the base material for the stent was chemically polished to remove a burr therefrom. Then a core metal for expanding the diameter of the base material for the stent was inserted into the base material for the stent. Thereby the outer diameter of the base material for the stent was increased to about 10 mm. Then the base material for the stent was heat-treated (and then air-cooled), with the core metal disposed in the base material for the stent. Thereby the expanded base material for the stent entirely having super-elasticity was prepared.

The expanded base material for the stent was mounted on the heat sink of the heat treatment apparatus having the construction shown in FIG. 14 to perform a selective annealing (plasticizing) of the connection parts.

A temperature control program was inputted to the computer (PC) serving as the controller shown in FIG. 14. In accordance with the program, an electric power was supplied from a DC power supply device to a partial annealing device (and to base material for the stent) through a lead wire. In dependence on a desired temperature and time period, a current value is set appropriately by using the program. Table 1 shows temperatures, time periods, and current values used to anneal the connection part.

TABLE 1

| Time (minute) | 0 (start of heating) | 20 | 25 | 30 | 95 | 135 | 135 | Finish of heating |
|---|---|---|---|---|---|---|---|---|
| Temperature (° C.) | 410 | 410 | 400 | 390 | 260 | 190 | 190 | Down to room temperature |
| Electric current | 6.3 | 6.3 | 6.2 | 6.1 | 4.7 | 3.9 | 3.9 | Air-cooling |

Where #: temperature dropped at the rate of about −10° C./5 minutes.

Electric current was applied to the base material for the stent to selectively heat the connection parts by self-heating joule heat). The temperature of the stent was kept at a high temperature (410° C.) for a certain period of time (20 minutes). The temperature dropped to 190° C. (heating current was gradually decreased) at the rate of about −10° C./5 minutes. Thereafter energizing was stopped to drop the temperature to the room temperature. Then the heat treatment finished.

As described above, the temperature of the connection part was measured by a non-contact type thermometer such as a thermography. The temperature is controlled by performing feed back of the data. Therefore the fluctuation (difference between set temperature and measured temperature) in the temperature during the heat treatment could be within ±2° C. This value is much smaller than temperature accuracy required for annealing treatment. Accordingly, the fluctuation in the temperature hardly affects the annealing treatment. The value of electric current required for heating is different according to various factors such as the design of the stent and the temperature of the cooling water.

It was possible to selectively plasticize and soften only the connection part of the base material for the stent by performing the above-described partial annealing. The bent portion of the zigzag line of the annular part was brought into contact with the heat sink to prevent the temperature of the bent portion of the zigzag line from rising. Therefore the bent portion of the zigzag line maintained the super-elasticity and the base material for the stent maintained its original expansion force and self-expandability.

The stent of the present invention to be implanted in a human body is made of a super-elastic metal formed approximately cylindrically and integrally and showing super-elasticity before and after the stent is inserted into the human body. The stent has a plurality of annular parts deformable in a direction in which an outer diameter thereof contracts, when a stress is applied thereto and a plurality of connection parts each connecting the adjacent annular parts to each other, with the annular parts arranged in an axial direction of the stent. Each of the annular parts is elastically deformable owing to super-elasticity thereof, whereas each of the connection parts is substantially a plastically deformable part (or a normal elastically deformable part)not super-elastic entirely or partly.

In the stent of the present invention, the annular part which is the expansion element is elastically deformable and capable of reliably expanding a lumen in the human body by its restoring force to its original diameter. Since only the connection part has the plastically deformable portion, the lumen-expanding function of the annular part is not inhibited. In conformity to a curve of the lumen, the plastically deformable portion of the connection part is plastically curved. Therefore a stress caused by the force of the stent of returning to its original straight shape is little applied to the lumen.

What is claimed is:

1. A method of producing a stent to be implanted in a human body, comprising:
    forming a base material for said stent having a plurality of annular parts deformable in a direction in which an outer diameter thereof contracts, when a stress is applied thereto and a plurality of connection parts each connecting said adjacent annular parts to each other, with said annular parts arranged in an axial direction of said stent, by partly removing a side surface of a prepared approximately cylindrical pipe, made of a super-elastic metal, having an outer diameter suitable for a portion of the human body in which said stent is implanted;
    heat-treating a part or an entirety of at least one of said connection parts of said base material for said stent to substantially eliminate super-elasticity of said at least one of said connection parts; and
    wherein said heat-treating comprises disposing said base material for said stent on a heat sink which has a plurality of concavities, with each annular part of said base material for said stent in contact with an outer surface of said heat sink, and with at least a portion of said at least one of said connection parts disposed over said concavities of said heat sink and not in contact with said outer surface of said heat sink, and energizing said entire base material for said stent so that said base material for said stent self-heats and said annular part in contact with said outer surface of said heat sink radiates heat.

2. A method according to claim 1, wherein said heat-treating is performed by heat generation caused by a resistance of said connection part owing to energization of both ends of said connection part.

3. A method according to claim 1, wherein said heat-treating is performed by heating an entirety or a portion of each of said connection parts to substantially eliminate super-elasticity thereof.

4. A method according to claim 1, wherein said concavities are formed between ring-shaped members, said ring-shaped members have a plurality of grooves formed on outer surfaces of said ring-shaped members, and said heat-treating is performed by disposing said connection parts of said base material for said stent on said grooves of said ring-shaped members.

5. A method of producing a stent to be implanted in a human body, comprising:
   forming a base material for said stent having a plurality of annular parts and a plurality of connection parts each connecting said adjacent annular parts to each other, with said annular parts arranged in an axial direction of said stent by preparing an approximately cylindrical metal pipe having an outer diameter smaller than an inner diameter of a portion in which said stent is implanted and having super-elasticity or a shape memory characteristic or to which said super-elasticity or said shape memory characteristic can be imparted and by partly removing a side surface of said pipe;
   forming an expanded mode of said base material for said stent by expanding said base material for said stent so that an outer diameter thereof becomes suitable for said portion in which said stent is implanted and by heat-setting said base material for said stent in an expanded state to store a configuration of said expanded base material for said stent and allow said super-elasticity to appear;
   heat-treating said expanded base material for said stent by heating an entirety or a portion of at least one of said connection parts to substantially eliminate super-elasticity thereof; and
   wherein said heat-treating comprises disposing said expanded base material for said stent on a heat sink which has a plurality of concavities, with each annular part of said base material for said stent in contact with an outer surface of said heat sink, and with at least a portion of said at least one of said connection parts disposed over said concavities of said heat sink and not in contact with said outer surface of said heat sink, and energizing said entire base material for said stent so that said base material for said stent self-heats and said annular part in contact with said outer surface of said heat sink radiates heat.

6. A method according to claim 5, wherein said heat-treating is performed by heating an entirety or a portion of each of said connection parts to substantially eliminate super-elasticity thereof.

7. A method according to claim 5, wherein said concavities are formed between ring-shaped members, said ring-shaped members have a plurality of grooves formed on outer surfaces of said ring-shaped members, and said heat-treating is performed by disposing said connection parts of said base material for said stent on said grooves of said ring-shaped members.

* * * * *